US006410826B1

(12) United States Patent
Yanofsky et al.

(10) Patent No.: US 6,410,826 B1
(45) Date of Patent: Jun. 25, 2002

(54) REDUCTION OF LIGNIN BIOSYNTHESIS IN TRANSGENIC PLANTS

(75) Inventors: Martin F. Yanofsky, San Diego; Sarah Liljegren, La Jolla; Cristina Ferrandiz, San Diego, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/339,998

(22) Filed: Jun. 25, 1999

Related U.S. Application Data

(60) Provisional application No. 60/090,649, filed on Jun. 25, 1998.

(51) Int. Cl.$^7$ .................. C12N 15/82; C12N 15/90; C12N 5/04; A01H 5/00; A01H 7/00
(52) U.S. Cl. .................. 800/278; 435/69.1; 435/468; 435/320.1; 800/287; 800/298; 800/313; 800/319
(58) Field of Search .................. 435/69.1, 320.1, 435/410, 419, 468; 800/278, 287, 290, 295, 298, 319, 313

(56) References Cited

PUBLICATIONS

Genbank Accession No. AAC19297.
Genbank Accession No. AF038863.
Genbank Accession No. AF038864.
Genbank Accession No. AF069299.
Genbank Accession No. AI486645.
Barceló, *International Rev. Cytology* 176:87–132 (1997).
Buxton and Redfearn, "Plant limitations to fiber digestion and utilization," *J. Nutr.* 127:814S–818S (1997).
Dixon et al., "Metabolic engineering: prospects for crop improvement through the genetic manipulation of phenylpropanoid biosynthesis and defense responses—a review," *Gene* 179:61–71 (1996).
Flanagan et al., "Specific expression of the AGL1 MADS–box gene suggests regulatory functions in *Arabidopsis* gynoecium and ovule development," *The Plant Journal* 10:343–353 (1996).
Gray–Mitsumune et al., "Developmentally regulated patterns of expression directed by popular PAL promoters in transgenic tobacco and popular," *Plant Mol. Biol.* 36:657–659 (1999).
Gu et al., "The Fruitfull MADS–box gene mediates cell differentiation during Arabidopsis fruit development," *Development* 125:1509–1517 (1998).
Hempel et al., "Floral determination and expression of floral regulatory genes in *Arabidopsis*," *Development* 124:3845–3853 (1997).
Kempin et al., "Targeted disruption in *Arabidopsis*," *Nature* 389:802–803 (1997).
Ma et al., "AGL1–AGL6, an *Arabidopsis* gene family with similarity to floral homeotic and transcription factor genes," *Genes & Development* 5:484–495 (1991).
Mandel and Yanofsky, "The Arabidopsis AGL8 MADS Box Gene is Expressed in Inflorescence Meristems and Is Negatively Regulated by APETALA1," *The Plant Cell* 7:1763–1771 (1995).
Menzel et al., "Identification of two MADS box genes that are expressed in the apical meristem of the long–day plant *Sinapis alba* in transition to flowering," *The Plant Journal* 9:399–408 (1996).
Mizukami et al., "Functional domains of the floral regulator Agamous: characterization of the DNA binding domain and analysis of dominant negative mutations," *Plant Cell* 8:831–845 (1996).
Purugganan et al., "Molecular Evolution of Flower Development: Diversification of the Plant MADS–Box Regulatory Gene Family," *Genetics* 140:345–356 (1995).
Riechmann and Meyerowitz, "MADS Domain Proteins in Plant Development," *Biol. Chem.* 378:1079–1101 (1997).
Savidge et al., "Temporal Relationship between the Transcription of Two–Arabidopsis MADS Box Genes and the Floral Organ Identity Genes," *The Plant Cell* 7:721–733 (1995).
Sundaresan et al., "Patterns of gene action in plant development revealed by enhancer trap and gene trap transposable elements," *Genes Devel.* 9:1797–1810 (1995).
Whetten and Sederoff, "Genetic engineering of wood," *Forest Ecology and Management* 43:301–316 (1991).
Yanofsky, Floral Meristems to Floral Organs: Genes Controlling Early Events in Arabidopsis Flower Development, *Annual Rev. Plant Physiol. Mol. Biol.* 46:167–188 (1995).
Yanofsky et al., "The protein encoded by the *Arabidopsis* homeotic gene agamous resembles transcription factors," *Nature* 346:35–39 (1990).

Primary Examiner—Gary Benzion
Assistant Examiner—Ashwin Mehta
(74) *Attorney, Agent, or Firm*—Townsend and Townsend and Crew LLP

(57) ABSTRACT

The present invention provides methods of selectively controlling lignin biosynthesis in plants such that lignification is reduced or enhanced, as desired. The invention provides, for example, a method of reducing lignification in a vascular plant by ectopically expressing a nucleic acid molecule encoding an AGL8-like gene product in the plant, whereby lignification is reduced due to ectopic expression of the nucleic acid molecule. An AGL8-like gene product useful in the invention can have, for example, substantially the amino acid sequence of an AGL8 ortholog such as Arabidopsis AGL8 (SEQ ID NO:2).

23 Claims, 12 Drawing Sheets

(4 of 12 Drawing Sheet(s) Filed in Color)

Figure 7

```
                                CCCAGAGAGACATAAGAAAGAAAGAGAGAGAGAGATACTT
            TGGTCATTTCAGGGTTGTCGTTTCTCTCTCTTGTTCTTGAGATTTTGAAGAGAGAGAT
  1 ATGGGAAGAGGTAGGGTTCAGCTGAAGAGGATAGAGAACAAGATCAATAGGCAAGTTACT
  1 M  G  R  G  R  V  Q  L  K  R  I  E  N  K  I  N  R  Q  V  T

61 TTCTCAAAGAGAAGGTCTGGTTTGCTCAAGAAAGCTCATGAGATCTCTGTTCTCTGCGAT
 21 F  S  K  R  R  S  G  L  L  K  K  A  H  E  I  S  V  L  C  D

121 GCTGAGGTTGCTCTCATCGTCTTCTCTTCCAAAGGCAAACTCTTCGAATATTCCACCGAC
 41 A  E  V  A  L  I  V  F  S  S  K  G  K  L  F  E  Y  S  T  D

181 TCTTGCATGGAGAGGATACTTGAACGCTATGATCGCTATTTATATTCAGACAAACAACTT
 61 S  C  M  E  R  I  L  E  R  Y  D  R  Y  L  Y  S  D  K  Q  L

241 GTTGGCCGAGACGTTTCACAAAGTGAAAATTGGGTTCTAGAACATGCTAAGCTCAAGGCA
 81 V  G  R  D  V  S  Q  S  E  N  W  V  L  E  H  A  K  L  K  A

301 AGAGTTGAGGTACTTGAGAAGAACAAAAGGAATTTTATGGGGGAAGATCTTGATTCGTTG
101 R  V  E  V  L  E  K  N  R  N  F  M  G  E  D  L  D  S  L

361 AGCTTGAAGGAGCTCCAAAGCTTGGAGCATCAGCTCGATGCAGCTATCAAGAGCATTAGG
121 S  L  K  E  L  Q  S  L  E  H  Q  L  D  A  A  I  K  S  I  R

421 TCAAGAAAGAACCAAGCTATGTTCGAATCCATATCTGCGCTCCAGAAGAAGGATAAAGCC
141 S  R  K  N  Q  A  M  F  E  S  I  S  A  L  Q  K  K  D  K  A

481 TTGCAAGATCACAACAATTCGCTTCTCAAAAAGATTAAGGAGAGGGAGAAGAAAACGGGT
161 L  Q  D  H  N  N  S  L  L  K  K  I  K  E  R  E  K  K  T  G

541 CAGCAAGAAGGACAATTAGTCCAATGCTCCAACTCTTCTTCAGTTCTTCTGCCTCAATAC
181 Q  Q  E  G  Q  L  V  Q  C  S  N  S  S  S  V  L  L  P  Q  Y

601 TGCGTAACCTCCTCCAGAGATGGCTTTGTGGAGAGAGTTGGGGGAGAGAACGGTGGTGCA
201 C  V  T  S  S  R  D  G  F  V  E  R  V  G  G  E  N  G  G  A

661 TCGTCGTTGACGGAACCAAACTCTCTGCTTCCGGCTTGGATGTTACGTCCTACCACTACG
221 S  S  L  T  E  P  N  S  L  L  P  A  W  M  L  R  P  T  T  T

721 AACGAGTAGAACTATCTCACTCTTTATAATATAATGATAATATAATTAATGTTTAATATT
241 N  E  *

781 TTCATAACATTCAGCATTTTTTTGGTGACTTATACTCATTATTAATACCGATATGTTTTA
841 GCTAGTCATATTATATGTATGATGGAACTCCGTTGTCGAGACGTATGTACGTAAGCTATC
901 ATTAGATTCACTGCGTCTTAAGAACAAAGATTCATATCTTGGTAATGATTTCTCATGAAA
961 TAn
```

```
                                                                  60
CCATCTACTA TCCGGTTGTT GACCCTTAAA GCTTTTGAAG ACTACTAGAA TAATGCAAAT

120
ACCATATGTC CATATCCATC CTTTTCTTTT GTTTGAACTG AACATTCTAA TTTTGTAAAA

180
GAAAAAACCT TATGTTAATA TCACCGTAGG CAAAAAAAAT ATCTCATCAT ATTAAATTTT

240
TATTATAAGA TTATACATTC TCTCGTTGTA AGAGTTACTC CAATTGCAAG TGTTGTATTA

300
ACTAATAAAA AGGACGAAAG TAGGAAGCTT ATAATTAATT GATGTTGCAT AGTACTGGTA

360
TATTGTTGAT GAATATAACA AGTATGAACA TTAATGCATG AAACGGGGTA TTTTGTCTTG

420
AACTCATTAA AGGCAATGTG AAAAGAAGAT GTGAGGTCTC ATTTTGAAAA TTTATCTTCT

480
AGCTTTGTCG ATTTTAAATC TATGAAATGA ACGCAACATA TAGAAATTTC ATGTGGACAA

540
CGACATTTAG ACGGTATCTT AATTAGACCG ATTAATTAGT AATATACTTA TATATATAAT

600
TAGTGGTGAT TATAAGTTTA CTTATCCACT TGAGAATTTA AACAATGGGC AATACCTTAA

660
TGTCGAAAGA AGCCGTCCCC ACTTCGTGTA ATGAGTTATG GGGAGAGAT CCTGTTAAAT

720
CGTCAAATAA AACAACTTAA GAACTAGAAA TTGACACCAA AAATCATAAA GAGAACGTTG

780
AAGAAGTCAT TTATCGTATC CAGCTCATAT TTCCTAGCTA AGATCAAATC AAGGCCGTTG

840
AAAGGGCTTG TAAGAAAATG TCGAAGAAAC CGTGGGGTTT AGAAGAAAGA CAAGAAATAG

900
AAGAACAATG ATGTTAAATT GCCTATTTTG GTGTATAGGA GTTGTCAAAA GAGGAGAGAG

960
AGAAGAAAAT TAGGTCAAAA TAATGAGCAC TAAAAATGGA GACATGTGTT GAGTAACTAT

1020
TACAAGAGCG ACTTATGCTT CCTTATGGCA ATGATATCCA AACCAAAGTG CAACGCTCCT

1080
TTTTTGCCCT AATTTCGTAA AGTCTCTCTC CTTCTTCGTC CTTAGGAAAA ACCCTAGAAA

1140
TTTAATCCCT TGTTCTTGAT CTTGCTTTTT GAGTAACCAT GATTTTGACC ACACACTATT

1200
TCTTCTATCT TTTGTGGTCT ATAGGATTTT GCTTTATATG TGTTTCTTGT ATTGCTCCGT
```

*FIG. 8A.*

```
                                                                   1260
ACGTACGTAT ACGAATTTAA ATGGTTATAA CAAGGTTTAT ATAAACTAGC ACAAATGAGT

1320
CCATGAAATT TGTTAGCGAA AAAGGTAGAA ATATATTGAG TCTTTAAACG GCAATATATA

1380
TAATTTTGCT GCAAAACTTA GCTTAATCA TGATCTAATG ATATTTCTT TAATTTCCTT

1440
TGCCAAATTA ATCACATGCA CGGATTTTTG GCAAGTTATG TGTCGAATTC TTCCATTCAC

1500
ACAACACTAA ACTTAATTAG AACTCTAGGA AATATTTTAA AATGACAACT TTATCGAAAA

1560
AAATTTAGTT ATGAAAACAA TTCCAGAATT AAACATGAGC TATATAATTT AAGATAAAAT

1620
GAAGTAATAT TGATATGTAT GTAATAACAT ATCTGATTGC GGTAAAAAAA AACATATCTG

1680
ATTAAATTGT TCATGCAGGC CCATGTCACT ATGATGTCAT CACGTTTTTA TTTTCACAAT

1740
AACTAATATA TATTCAAAAA AATAGTTTTG TCAGATTAAA TTTTTTTTGG TGGTCAGCTT

1800
TCTCCAACCT ACTAAACTAG TTTGGAATGT TCTCTTCTTT ATTTTTCTTT TTCTTGATTT

1860
CTTATGTTTT TTATTTATGG AATTTTAAGA CGGATTGTTT AGGTCGTTTC TCTCTTTTCT

1920
TGTTTTCTAA AGTTACTTTT GTAAACTCAT CTCCTCCCAA TTAGACAGTC AATCATATAG

1980
TTATCTTTTA ATATATGTCT AGTTGATAAA AAAAATGAAA AAATACTGGT GGTAGTTCTA

2040
CTAATGTTTG TGTAAAAAAT CTGATATTAT GAATCTAATC AATTTCTTTG ATCGTATAAT

2100
GTGGGTTAAA TTTAGTAATT TTTTACATAA ATAAGAACTG TAATGTTGAT GTATATTGGG

2160
GAATCAGTAT ATTAGCTTGG GTAACTATAC TTCTGGAAAT ACTTGAAGAT TTAACTATTT

2220
GCAAAATTAT AATTTAGTCC CGAAAAATAC AGACGACGGG ACACGACAAC ATATAAGCAG

2280
GTTTGAATCT TGGAAAATTT TGTATACATA ACCTATATAA ATACTAATGT TCTGGTTGGG

2340
TTCAAAAGCC TTTTCAAAAG TTCCATTTTT TAAATTCAAG GACATTTTAC ATAGGAAATA

2400
AGTTGAGTCA TAAAAAATAA TGGTTATTTT GTAAGGTTTT TTTTTTGATT AAAACGCACA

2460
TATTAAGAAG TTAGTTTTTT TTCACTACCA AATATCAATT AATTTAAAAC CATGCAACCA
```

FIG. 8B.

```
                                                                    2520
TTCATAAAAC AATACTATTA AAGAATATAA ATAATCACAA AATATTAAAT ACACTTAAAA

2580
TTTACATATA AATTTACAAA ACATCTAATT AATTGAAACA GAAAGGAAAA GGTAAAATAT

2640
ATCATAAAAT GAGACATATA TCCTATAAAA AAAAAATGAG GCATATGAAG TAAATAATAA

2700
GAGACATGCA TGTAAGCATT CGGTTAATTA ATCGAGTCAA AGATATATAT CAGTAAATAC

2760
ATATGTGTAT ATTTCTGGAA AAAGAATATA TATATTGAGA AATAAGAAAA GATGAAAATG
                                                                    M>

2820
GAAAATGGTA TGTATAAAAA GAAAGGAGTG TGCGACTCTT GTGTCTCGTC CAAAAGCAGA
 E   N  G   M  Y  K  K   K  G  V   C  D  S    C  V  S    K  S  R>

2880
TCCAACCACA GCCCCAAAAG AAGCATGATG GAGCCTCAGC CTCACCATCT CCTCATGGAT
 S  N  H    S  P  K  R  S  M  M   E  P  Q    P  H  H  L  L  M  D>

2940
TGGAACAAAG CTAATGATCT TCTCACACAA GAACACGCAG CTTTTCTCAA TGATCCTCAC
 W  N  K    A  N  D  L  L  T  Q   E  H  A    A  F  L  N  D  P  H>

3000
CATCTCATGT TAGATCCACC TCCCGAAACC CTAATTCACT TGGACGAAGA CGAAGAGTAC
 H  L  M    L  D  P  P  P  E  T   L  I  H    L  D  E  D  E  E  Y>

3060
GATGAAGACA TGGATGCGAT GAAGGAGATG CAGTACATGA TCGCCGTCAT GCAGCCCGTA
 D  E  D    M  D  A  M  K  E  M   Q  Y  M    I  A  V  M  Q  P  V>

3120
GACATCGACC CTGCCACGGT CCCTAAGCCG AACCGCCGTA ACGTAAGGAT AAGCGACGAT
 D  I  D    P  A  T  V  P  K  P   N  R  R    N  V  R  I  S  D  D>

3180
CCTCAGACGG TGGTTGCTCG TCGGCGTCGG GAAAGGATCA GCGAGAAGAT CCGAATTCTC
 P  Q  T    V  V  A  R  R  R  R   E  R  I    S  E  K  I  R  I  L>

3240
AAGAGGATCG TGCCTGGTGG TGCGAAGATG GACACAGCTT CCATGCTCGA CGAAGCCATA
 K  R  I    V  P  G  G  A  K  M   D  T  A    S  M  L  D  E  A  I>

3300
CGTTACACCA AGTTCTTGAA ACGGCAGGTG AGGATTCTTC AGCCTCACTC TCAGATTGGA
 R  Y  T    K  F  L  K  R  Q  V   R  I  L    Q  P  H  S  Q  I  G>

3360
GCTCCTATGG CTAACCCCTC TTACCTTTGT TATTACCACA ACTCCCAACC CTGATGAACT
 A  P  M    A  N  P  S  Y  L  C   Y  Y  H    N  S  Q  P  *>

3420
ACACAGAAGC TCGCTAGCTA GACATTTGGT GTCATCCTCT CAACCTTTTT CATGTTGATA

3480
TATTATATAT AGATGCATAA AGATTCGATC CAAGATTGTA TGGGTGTTTT AATATTATTA
```

*FIG. 8C.*

```
                                                                    3540
TTCTAAGATA TATGATGTAC AATTGTGTAC CAAGTTTCTT TATCTTGATA TCATATGCAT
                                                                    3600
AAATAATTGG TGAATAAAAA GAAGATATTG ATTGTAAACA AAAAAAAGAA GATATTGATT
                                                                    3660
GTTAATTAGG GTTTGATCAT TCTGTATGAA AGCTTTGGCC TGCAAATTAA TTTTCGATAT
                                                                    3720
ATATATATAT ATATGGAGAA TATATATCAA ATACTTTTTT AATTTGACTA TAATTTGTAT
                                                                    3780
CAATTATCTG AATCTGATGA GTGTAGGTTA TATATGGATT AGCAAAAAAG AAAACAACCA
                                                                    3840
TTATTACGCA CCTACATTAA AAATCATCCA CCAAAGAAGA AACCATCCTC AAGAGGGTTC
CC
```

FIG. 8D.

SEQUENCE LISTING

<160> NUMBER OF SEQ ID NOS: 23

<210> SEQ ID NO 1
<211> LENGTH: 1062
<212> TYPE: DNA
<213> ORGANISM: Arabidopsis thaliana
<220> FEATURE:
<221> NAME/KEY: CDS
<222> LOCATION: (101)..(826)

<400> SEQUENCE: 1

```
cccagagaga cataagaaag aaagagagag agagatactt tggtcatttc agggttgtcg      60
tttctctctc ttgttcttga gattttgaag agagagagat atg gga aga ggt agg      115
                                             Met Gly Arg Gly Arg
                                              1               5 gtt cag ctg aag agg ata gag aac aag atc aat agg caa gtt act ttc      163
Val Gln Leu Lys Arg Ile Glu Asn Lys Ile Asn Arg Gln Val Thr Phe
            10                  15                  20 tca aag aga agg tct ggt ttg ctc aag aaa gct cat gag atc tct gtt      211
Ser Lys Arg Arg Ser Gly Leu Leu Lys Lys Ala His Glu Ile Ser Val
        25                  30                  35 ctc tgc gat gct gag gtt gct ctc atc gtc ttc tct tcc aaa ggc aaa      259
Leu Cys Asp Ala Glu Val Ala Leu Ile Val Phe Ser Ser Lys Gly Lys
    40                  45                  50 ctc ttc gaa tat tcc acc gac tct tgc atg gag agg ata ctt gaa cgc      307
Leu Phe Glu Tyr Ser Thr Asp Ser Cys Met Glu Arg Ile Leu Glu Arg
55                  60                  65 tat gat cgc tat tta tat tca gac aaa caa ctt gtt ggc cga gac gtt      355
Tyr Asp Arg Tyr Leu Tyr Ser Asp Lys Gln Leu Val Gly Arg Asp Val
 70                  75                  80                  85 tca caa agt gaa aat tgg gtt cta gaa cat gct aag ctc aag gca aga      403
Ser Gln Ser Glu Asn Trp Val Leu Glu His Ala Lys Leu Lys Ala Arg
                90                  95                 100 gtt gag gta ctt gag aag aac aaa agg aat ttt atg ggg gaa gat ctt      451
Val Glu Val Leu Glu Lys Asn Lys Arg Asn Phe Met Gly Glu Asp Leu
            105                 110                 115 gat tcg ttg agc ttg aag gag ctc caa agc ttg gag cat cag ctc gat      499
Asp Ser Leu Ser Leu Lys Glu Leu Gln Ser Leu Glu His Gln Leu Asp
        120                 125                 130 gca gct atc aag agc att agg tca aga aag aac caa gct atg ttc gaa      547
Ala Ala Ile Lys Ser Ile Arg Ser Arg Lys Asn Gln Ala Met Phe Glu
    135                 140                 145 tcc ata tct gcg ctc cag aag aag gat aaa gcc ttg caa gat cac aac      595
Ser Ile Ser Ala Leu Gln Lys Lys Asp Lys Ala Leu Gln Asp His Asn
150                 155                 160                 165 aat tcg ctt ctc aaa aag att aag gag agg gag aag aaa acg ggt cag      643
Asn Ser Leu Leu Lys Lys Ile Lys Glu Arg Glu Lys Lys Thr Gly Gln
                170                 175                 180 caa gaa gga caa tta gtc caa tgc tcc aac tct tct tca gtt ctt ctg      691
Gln Glu Gly Gln Leu Val Gln Cys Ser Asn Ser Ser Ser Val Leu Leu
            185                 190                 195 cct caa tac tgc gta acc tcc tcc aga gat ggc ttt gtg gag aga gtt      739
Pro Gln Tyr Cys Val Thr Ser Ser Arg Asp Gly Phe Val Glu Arg Val
        200                 205                 210 ggg gga gag aac ggt ggt gca tcg tcg ttg acg gaa cca aac tct ctg      787
Gly Gly Glu Asn Gly Gly Ala Ser Ser Leu Thr Glu Pro Asn Ser Leu
    215                 220                 225 ctt ccg gct tgg atg tta cgt cct acc act acg aac gag tagaactatc      836
Leu Pro Ala Trp Met Leu Arg Pro Thr Thr Thr Asn Glu
230                 235                 240 tcactcttta taatataatg ataatataat taatgtttaa tattttcata acattcagca      896 ttttttggt gacttatact cattattaat accgatatgt tttagctagt catattatat       956
gtatgatgga actccgttgt cgagacgtat gtacgtaagc tatcattaga ttcactgcgt     1016
cttaagaaca aagattcata tcttggtaat gatttctcat gaaata                   1062
```

<210> SEQ ID NO 2

```
<211> LENGTH: 242
<212> TYPE: PRT
<213> ORGANISM: Arabidopsis thaliana

<400> SEQUENCE: 2

Met Gly Arg Gly Arg Val Gln Leu Lys Arg Ile Glu Asn Lys Ile Asn
 1               5                  10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Ala Leu Ile Val Phe
        35                  40                  45

Ser Ser Lys Gly Lys Leu Phe Glu Tyr Ser Thr Asp Ser Cys Met Glu
    50                  55                  60

Arg Ile Leu Glu Arg Tyr Asp Arg Tyr Leu Tyr Ser Asp Lys Gln Leu
65                  70                  75                  80

Val Gly Arg Asp Val Ser Gln Ser Glu Asn Trp Val Leu Glu His Ala
                85                  90                  95

Lys Leu Lys Ala Arg Val Glu Val Leu Glu Lys Asn Lys Arg Asn Phe
            100                 105                 110

Met Gly Glu Asp Leu Asp Ser Leu Ser Leu Lys Glu Leu Gln Ser Leu
        115                 120                 125

Glu His Gln Leu Asp Ala Ala Ile Lys Ser Ile Arg Ser Arg Lys Asn
    130                 135                 140

Gln Ala Met Phe Glu Ser Ile Ser Ala Leu Gln Lys Lys Asp Lys Ala
145                 150                 155                 160

Leu Gln Asp His Asn Asn Ser Leu Leu Lys Lys Ile Lys Glu Arg Glu
                165                 170                 175

Lys Lys Thr Gly Gln Gln Glu Gly Gln Leu Val Gln Cys Ser Asn Ser
            180                 185                 190

Ser Ser Val Leu Leu Pro Gln Tyr Cys Val Thr Ser Ser Arg Asp Gly
        195                 200                 205

Phe Val Glu Arg Val Gly Gly Glu Asn Gly Gly Ala Ser Ser Leu Thr
    210                 215                 220

Glu Pro Asn Ser Leu Leu Pro Ala Trp Met Leu Arg Pro Thr Thr Thr
225                 230                 235                 240

Asn Glu

<210> SEQ ID NO 3
<211> LENGTH: 896
<212> TYPE: DNA
<213> ORGANISM: Arabidopsis thaliana
<220> FEATURE:
<221> NAME/KEY: CDS
<222> LOCATION: (7)..(753)

<400> SEQUENCE: 3 ggatca atg gag gaa ggt ggg agt agt cac gac gca gag agt agc aag        48
       Met Glu Glu Gly Gly Ser Ser His Asp Ala Glu Ser Ser Lys
        1               5                  10 aaa cta ggg aga ggg aaa ata gag ata aag agg ata gag aac aca aca        96
Lys Leu Gly Arg Gly Lys Ile Glu Ile Lys Arg Ile Glu Asn Thr Thr
 15                  20                  25                  30 aat cgt caa gtt act ttc tgc aaa cga cgc aat ggt ctt ctc aag aaa       144
Asn Arg Gln Val Thr Phe Cys Lys Arg Arg Asn Gly Leu Leu Lys Lys
                35                  40                  45 gct tat gaa ctc tct gtc ttg tgt gat gcc gaa gtt gcc ctc gtc atc       192
Ala Tyr Glu Leu Ser Val Leu Cys Asp Ala Glu Val Ala Leu Val Ile
            50                  55                  60
```

-continued

```
ttc tcc act cgt ggc cgt ctc tat gag tac gcc aac aac agt gtg agg         240
Phe Ser Thr Arg Gly Arg Leu Tyr Glu Tyr Ala Asn Asn Ser Val Arg
            65                  70                  75 ggt aca att gaa agg tac aag aaa gct tgt tcc gat gcc gtc aac cct         288
Gly Thr Ile Glu Arg Tyr Lys Lys Ala Cys Ser Asp Ala Val Asn Pro
        80                  85                  90 cct tcc gtc acc gaa gct aat act cag tac tat cag caa gaa gcc tct         336
Pro Ser Val Thr Glu Ala Asn Thr Gln Tyr Tyr Gln Gln Glu Ala Ser
 95                 100                 105                 110 aag ctt cgg agg cag att cga gat att cag aat tca aat agg cat att         384
Lys Leu Arg Arg Gln Ile Arg Asp Ile Gln Asn Ser Asn Arg His Ile
                115                 120                 125 gtt ggg gaa tca ctt ggt tcc ttg aac ttc aag gaa ctc aaa aac cta         432
Val Gly Glu Ser Leu Gly Ser Leu Asn Phe Lys Glu Leu Lys Asn Leu
            130                 135                 140 gaa gga cgt ctt gaa aaa gga atc agc cgt gtc cgc tcc aaa aag aat         480
Glu Gly Arg Leu Glu Lys Gly Ile Ser Arg Val Arg Ser Lys Lys Asn
        145                 150                 155 gag ctg tta gtg gca gag ata gag tat atg cag aag agg gaa atg gag         528
Glu Leu Leu Val Ala Glu Ile Glu Tyr Met Gln Lys Arg Glu Met Glu
    160                 165                 170 ttg caa cac aat aac atg tac ctg cga gca aag ata gcc gaa ggc gcc         576
Leu Gln His Asn Asn Met Tyr Leu Arg Ala Lys Ile Ala Glu Gly Ala
175                 180                 185                 190 aga ttg aat ccg gac cag cag gaa tcg agt gtg ata caa ggg acg aca         624
Arg Leu Asn Pro Asp Gln Gln Glu Ser Ser Val Ile Gln Gly Thr Thr
                195                 200                 205 gtt tac gaa tcc ggt gta tct tct cat gac cag tcg cag cat tat aat         672
Val Tyr Glu Ser Gly Val Ser Ser His Asp Gln Ser Gln His Tyr Asn
            210                 215                 220 cgg aac tat att ccg gtg aac ctt ctt gaa ccg aat cag caa ttc tcc         720
Arg Asn Tyr Ile Pro Val Asn Leu Leu Glu Pro Asn Gln Gln Phe Ser
        225                 230                 235 ggc caa gac caa cct cct ctt caa ctt gtg taa ctcaaaacat gataacttgt      773
Gly Gln Asp Gln Pro Pro Leu Gln Leu Val
    240                 245 ttcttcccct cataacgatt aagagagaga cgagagagtt catttttatat ttataacgcg     833 actgtgtatt catagtttag gttctaataa tgataataac aaaactgttg tttctttgct     893
tca                                                                    896

<210> SEQ ID NO 4
<211> LENGTH: 248
<212> TYPE: PRT
<213> ORGANISM: Arabidopsis thaliana

<400> SEQUENCE: 4

Met Glu Glu Gly Gly Ser Ser His Asp Ala Glu Ser Ser Lys Lys Leu
 1               5                  10                  15

Gly Arg Gly Lys Ile Glu Ile Lys Arg Ile Glu Asn Thr Thr Asn Arg
            20                  25                  30

Gln Val Thr Phe Cys Lys Arg Arg Asn Gly Leu Leu Lys Lys Ala Tyr
        35                  40                  45

Glu Leu Ser Val Leu Cys Asp Ala Glu Val Ala Leu Val Ile Phe Ser
    50                  55                  60

Thr Arg Gly Arg Leu Tyr Glu Tyr Ala Asn Asn Ser Val Arg Gly Thr
65                  70                  75                  80

Ile Glu Arg Tyr Lys Lys Ala Cys Ser Asp Ala Val Asn Pro Pro Ser
```

```
                    85                  90                  95
Val Thr Glu Ala Asn Thr Gln Tyr Tyr Gln Gln Glu Ala Ser Lys Leu
            100                 105                 110

Arg Arg Gln Ile Arg Asp Ile Gln Asn Ser Asn Arg His Ile Val Gly
        115                 120                 125

Glu Ser Leu Gly Ser Leu Asn Phe Lys Glu Leu Lys Asn Leu Glu Gly
    130                 135                 140

Arg Leu Glu Lys Gly Ile Ser Arg Val Arg Ser Lys Lys Asn Glu Leu
145                 150                 155                 160

Leu Val Ala Glu Ile Glu Tyr Met Gln Lys Arg Glu Met Glu Leu Gln
                165                 170                 175

His Asn Asn Met Tyr Leu Arg Ala Lys Ile Ala Glu Gly Ala Arg Leu
            180                 185                 190

Asn Pro Asp Gln Gln Glu Ser Ser Val Ile Gln Gly Thr Thr Val Tyr
        195                 200                 205

Glu Ser Gly Val Ser Ser His Asp Gln Ser Gln His Tyr Asn Arg Asn
    210                 215                 220

Tyr Ile Pro Val Asn Leu Leu Glu Pro Asn Gln Gln Phe Ser Gly Gln
225                 230                 235                 240

Asp Gln Pro Pro Leu Gln Leu Val
                245

<210> SEQ ID NO 5
<211> LENGTH: 959
<212> TYPE: DNA
<213> ORGANISM: Arabidopsis thaliana
<220> FEATURE:
<221> NAME/KEY: CDS
<222> LOCATION: (78)..(818)

<400> SEQUENCE: 5
gaattcatct tcccatcctc acttctcttt ctttctgatc ataattaatc ttgctaagcc      60
agctagggct tatagaa atg gag ggt ggt gcg agt aat gaa gta gca gag          110
                   Met Glu Gly Gly Ala Ser Asn Glu Val Ala Glu
                    1               5                  10 agc agc aag aag ata ggg aga ggg aag ata gag ata aag agg ata gag        158
Ser Ser Lys Lys Ile Gly Arg Gly Lys Ile Glu Ile Lys Arg Ile Glu
            15                  20                  25 aac act acg aat cgt caa gtc act ttc tgc aaa cga cgc aat ggt tta        206
Asn Thr Thr Asn Arg Gln Val Thr Phe Cys Lys Arg Arg Asn Gly Leu
    30                  35                  40 ctc aag aaa gct tat gag ctc tct gtc ttg tgt gac gct gag gtt gct        254
Leu Lys Lys Ala Tyr Glu Leu Ser Val Leu Cys Asp Ala Glu Val Ala
45                  50                  55 ctt gtc atc ttc tcc act cga ggc cgt ctc tac gag tac gcc aac aac        302
Leu Val Ile Phe Ser Thr Arg Gly Arg Leu Tyr Glu Tyr Ala Asn Asn
        60                  65                  70                  75 agt gtg aga gga aca ata gaa agg tac aag aaa gct tgc tcc gac gcc        350
Ser Val Arg Gly Thr Ile Glu Arg Tyr Lys Lys Ala Cys Ser Asp Ala
                80                  85                  90 gtt aac cct ccg acc atc acc gaa gct aat act cag tac tat cag caa        398
Val Asn Pro Pro Thr Ile Thr Glu Ala Asn Thr Gln Tyr Tyr Gln Gln
            95                 100                 105 gag gcg tct aaa ctc cgg aga cag att cgg gac att cag aat ttg aac        446
Glu Ala Ser Lys Leu Arg Arg Gln Ile Arg Asp Ile Gln Asn Leu Asn
        110                 115                 120 aga cac att ctt ggt gaa tct ctt ggt tcc ttg aac ttt aag gaa ctc        494
Arg His Ile Leu Gly Glu Ser Leu Gly Ser Leu Asn Phe Lys Glu Leu
```

```
              125                 130                 135
aag aac ctt gaa agt agg ctt gag aaa gga atc agt cgt gtc cga tcc        542
Lys Asn Leu Glu Ser Arg Leu Glu Lys Gly Ile Ser Arg Val Arg Ser
140                 145                 150                 155 aag aag cac gag atg tta gtt gca gag att gaa tac atg caa aaa agg        590
Lys Lys His Glu Met Leu Val Ala Glu Ile Glu Tyr Met Gln Lys Arg
                160                 165                 170 gaa atc gag ctg caa aac gat aac atg tat ctc cgc tcc aag att act        638
Glu Ile Glu Leu Gln Asn Asp Asn Met Tyr Leu Arg Ser Lys Ile Thr
            175                 180                 185 gaa aga aca ggt cta cag caa caa gaa tcg agt gtg ata cat caa ggg        686
Glu Arg Thr Gly Leu Gln Gln Gln Glu Ser Ser Val Ile His Gln Gly
        190                 195                 200 aca gtt tac gag tcg ggt gtt act tct tct cac cag tcg ggg cag tat        734
Thr Val Tyr Glu Ser Gly Val Thr Ser Ser His Gln Ser Gly Gln Tyr
    205                 210                 215 aac cgg aat tat att gcg gtt aac ctt ctt gaa ccg aat cag aat tcc        782
Asn Arg Asn Tyr Ile Ala Val Asn Leu Leu Glu Pro Asn Gln Asn Ser
220                 225                 230                 235 tcc aac caa gac caa cca cct ctg caa ctt gtt tga ttcagtctaa             828
Ser Asn Gln Asp Gln Pro Pro Leu Gln Leu Val
                240                 245 cataagcttc tttcctcagc ctgagatcga tctatagtgt cacctaaatg cggccgcgtc      888
cctcaacatc tagtcgcaag ctgaggggaa ccactagtgt catacgaacc tccaagagac      948
ggttacacaa a                                                           959

<210> SEQ ID NO 6
<211> LENGTH: 246
<212> TYPE: PRT
<213> ORGANISM: Arabidopsis thaliana

<400> SEQUENCE: 6

Met Glu Gly Gly Ala Ser Asn Glu Val Ala Glu Ser Ser Lys Lys Ile
 1               5                  10                  15

Gly Arg Gly Lys Ile Glu Ile Lys Arg Ile Glu Asn Thr Thr Asn Arg
                20                  25                  30

Gln Val Thr Phe Cys Lys Arg Arg Asn Gly Leu Leu Lys Lys Ala Tyr
            35                  40                  45

Glu Leu Ser Val Leu Cys Asp Ala Glu Val Ala Leu Val Ile Phe Ser
        50                  55                  60

Thr Arg Gly Arg Leu Tyr Glu Tyr Ala Asn Asn Ser Val Arg Gly Thr
65                  70                  75                  80

Ile Glu Arg Tyr Lys Lys Ala Cys Ser Asp Ala Val Asn Pro Pro Thr
                85                  90                  95

Ile Thr Glu Ala Asn Thr Gln Tyr Tyr Gln Gln Glu Ala Ser Lys Leu
            100                 105                 110

Arg Arg Gln Ile Arg Asp Ile Gln Asn Leu Asn Arg His Ile Leu Gly
        115                 120                 125

Glu Ser Leu Gly Ser Leu Asn Phe Lys Glu Leu Lys Asn Leu Glu Ser
    130                 135                 140

Arg Leu Glu Lys Gly Ile Ser Arg Val Arg Ser Lys Lys His Glu Met
145                 150                 155                 160

Leu Val Ala Glu Ile Glu Tyr Met Gln Lys Arg Glu Ile Glu Leu Gln
                165                 170                 175

Asn Asp Asn Met Tyr Leu Arg Ser Lys Ile Thr Glu Arg Thr Gly Leu
            180                 185                 190
```

```
Gln Gln Gln Glu Ser Ser Val Ile His Gln Gly Thr Val Tyr Glu Ser
            195                 200                 205

Gly Val Thr Ser Ser His Gln Ser Gly Gln Tyr Asn Arg Asn Tyr Ile
    210                 215                 220

Ala Val Asn Leu Leu Glu Pro Asn Gln Asn Ser Ser Asn Gln Asp Gln
225                 230                 235                 240

Pro Pro Leu Gln Leu Val
                245

<210> SEQ ID NO 7
<211> LENGTH: 3842
<212> TYPE: DNA
<213> ORGANISM: Arabidopsis thaliana
<220> FEATURE:
<221> NAME/KEY: CDS
<222> LOCATION: (2758)..(3354)

<400> SEQUENCE: 7
ccatctacta tccggttgtt gacccttaaa gcttttgaag actactagaa taatgcaaat     60
accatatgtc catatccatc cttttctttt gtttgaactg aacattctaa ttttgtaaaa    120
gaaaaaacct tatgttaata tcaccgtagg caaaaaaaat atctcatcat attaaatttt    180
tattataaga ttatacattc tctcgttgta agagttactc caattgcaag tgttgtatta    240
actaataaaa aggacgaaag taggaagctt ataattaatt gatgttgcat agtactggta    300
tattgttgat gaatataaca agtatgaaca ttaatgcatg aaacggggta ttttgtcttg    360
aactcattaa aggcaatgtg aaagaagat gtgaggtctc attttgaaaa tttatcttct    420
agctttgtcg attttaaatc tatgaaatga acgaacata tagaaatttc atgtggacaa    480
cgacatttag acggtatctt aattagaccg attaattagt aatatactta tatatataat    540
tagtggtgat tataagttta cttatccact tgagaattta acaatgggc aataccttaa    600 tgtcgaaaga agccgtcccc acttcgtgta atgagttatg ggggagagat cctgttaaat    660
cgtcaaataa aacaacttaa gaactagaaa ttgacaccaa aaatcataaa gagaacgttg    720
aagaagtcat ttatcgtatc cagctcatat ttcctagcta agatcaaatc aaggccgttg    780
aaagggcttg taagaaaatg tcgaagaaac cgtgggggttt agaagaaaga caagaaatag    840
aagaacaatg atgttaaatt gcctatttg gtgtatagga gttgtcaaaa gaggagagag    900
agaagaaaat taggtcaaaa taatgagcac taaaatgga gacatgtgtt gagtaactat    960
tacaagagcg acttatgctt ccttatggca atgatatcca aaccaaagtg caacgctcct   1020 ttttgccct aatttcgtaa agtctctctc cttcttcgtc cttaggaaaa accctagaaa   1080
tttaatccct tgttcttgat cttgcttttt gagtaaccat gattttgacc acacactatt   1140
tcttctatct tttgtggtct ataggatttt gctttatatg tgtttcttgt attgctccgt   1200
acgtacgtat acgaatttaa atggttataa caaggtttat ataaactagc acaaatgagt   1260
ccatgaaatt tgttagcgaa aaaggtagaa atatattgag tctttaaacg gcaatatata   1320
taattttgct gcaaaactta gctttaatca tgatctaatg atatttctt taatttcctt   1380 tgccaaatta atcacatgca cggattttg gcaagttatg tgtcgaattc ttccattcac   1440
acaacactaa acttaattag aactctagga aatatttaa aatgacaact ttatcgaaaa   1500
aaatttagtt atgaaaacaa ttccagaatt aaacatgagc tatataattt aagataaat    1560 gaagtaatat tgatatgtat gtaataacat atctgattgc ggtaaaaaaa aacatatctg   1620 attaaaattgt tcatgcaggc ccatgtcact atgatgtcat cacgttttta ttttcacaat   1680
```

```
aactaatata tattcaaaaa aatagttttg tcagattaaa ttttttttgg tggtcagctt    1740
tctccaacct actaaactag tttggaatgt tctcttcttt atttttcctt ttcttgattt    1800
cttatgtttt ttatttatgg aattttaaga cggattgttt aggtcgtttc tctcttttct    1860
tgttttctaa agttactttt gtaaactcat ctcctcccaa ttagacagtc aatcatatag    1920
ttatctttta atatatgtct agttgataaa aaaaaatgaa aaatactggt ggtagttcta    1980
ctaatgtttg tgtaaaaaat ctgatattat gaatctaatc aatttctttg atcgtataat    2040
gtgggttaaa tttagtaatt ttttacataa ataagaactg taatgttgat gtatattggg    2100
gaatcagtat attagcttgg gtaactatac ttctggaaat acttgaagat ttaactattt    2160
gcaaaattat aatttagtcc cgaaaaatac agacgacggg acacgacaac atataagcag    2220
gtttgaatct tggaaaattt tgtatacata acctatataa atactaatgt tctggttggg    2280
ttcaaaagcc ttttcaaaag ttccatttt  taaattcaag acattttac  ataggaaata    2340 agttgagtca taaaaaataa tggttatttt gtaaggtttt ttttttgatt aaaacgcaca    2400
tattaagaag ttagtttttt ttcactacca aatatcaatt aattttaaac catgcaacca    2460
ttcataaaac aatactatta aagaatataa ataatcacaa aatattaaat acacttaaaa    2520
tttacatata aatttacaaa acatctaatt aattgaaaca gaaaggaaaa ggtaaaatat    2580
atcataaaat gagacatata tcctataaaa aaaaaatgag gcatatgaag taaataataa    2640
gagacatgca tgtaagcatt cggttaatta atcgagtcaa agatatatat cagtaaaatac   2700 atatgtgtat atttctggaa aaagaatata tatattgaga aataagaaaa gatgaaa       2757
```

```
atg gaa aat ggt atg tat aaa aag aaa gga gtg tgc gac tct tgt gtc    2805
Met Glu Asn Gly Met Tyr Lys Lys Lys Gly Val Cys Asp Ser Cys Val
 1               5                  10                  15 tcg tcc aaa agc aga tcc aac cac agc ccc aaa aga agc atg atg gag    2853
Ser Ser Lys Ser Arg Ser Asn His Ser Pro Lys Arg Ser Met Met Glu
             20                  25                  30 cct cag cct cac cat ctc ctc atg gat tgg aac aaa gct aat gat ctt    2901
Pro Gln Pro His His Leu Leu Met Asp Trp Asn Lys Ala Asn Asp Leu
         35                  40                  45 ctc aca caa gaa cac gca gct ttt ctc aat gat cct cac cat ctc atg    2949
Leu Thr Gln Glu His Ala Ala Phe Leu Asn Asp Pro His His Leu Met
 50                  55                  60 tta gat cca cct ccc gaa acc cta att cac ttg gac gaa gac gaa gag    2997
Leu Asp Pro Pro Pro Glu Thr Leu Ile His Leu Asp Glu Asp Glu Glu
 65                  70                  75                  80 tac gat gaa gac atg gat gcg atg aag gag atg cag tac atg atc gcc    3045
Tyr Asp Glu Asp Met Asp Ala Met Lys Glu Met Gln Tyr Met Ile Ala
                 85                  90                  95 gtc atg cag ccc gta gac atc gac cct gcc acg gtc cct aag ccg aac    3093
Val Met Gln Pro Val Asp Ile Asp Pro Ala Thr Val Pro Lys Pro Asn
            100                 105                 110 cgc cgt aac gta agg ata agc gac gat cct cag acg gtg gtt gct cgt    3141
Arg Arg Asn Val Arg Ile Ser Asp Asp Pro Gln Thr Val Val Ala Arg
        115                 120                 125 cgg cgt cgg gaa agg atc agc gag aag atc cga att ctc aag agg atc    3189
Arg Arg Arg Glu Arg Ile Ser Glu Lys Ile Arg Ile Leu Lys Arg Ile
130                 135                 140 gtg cct ggt ggt gcg aag atg gac aca gct tcc atg ctc gac gaa gcc    3237
Val Pro Gly Gly Ala Lys Met Asp Thr Ala Ser Met Leu Asp Glu Ala
145                 150                 155                 160 ata cgt tac acc aag ttc ttg aaa cgg cag gtg agg att ctt cag cct    3285
Ile Arg Tyr Thr Lys Phe Leu Lys Arg Gln Val Arg Ile Leu Gln Pro
```

```
                      165                 170                 175
cac tct cag att gga gct cct atg gct aac ccc tct tac ctt tgt tat    3333
His Ser Gln Ile Gly Ala Pro Met Ala Asn Pro Ser Tyr Leu Cys Tyr
            180                 185                 190 tac cac aac tcc caa ccc tga tgaactacac agaagctcgc tagctagaca        3384
Tyr His Asn Ser Gln Pro
        195 tttggtgtca tcctctcaac cttttttcatg ttgatatatt atatatagat gcataaagat  3444 tcgatccaag attgtatggg tgttttaata ttattattct aagatatatg atgtacaatt  3504 gtgtaccaag tttctttatc ttgatatcat atgcataaat aattggtgaa taaaaagaag  3564 atattgattg taaacaaaaa aaagaagata ttgattgtta attagggttt gatcattctg  3624 tatgaaagct ttggcctgca aattaattt cgatatatat atatatatat ggagaatata  3684 tatcaaatac ttttttaatt tgactataat ttgtatcaat tatctgaatc tgatgagtgt  3744 aggttatata tggattagca aaaagaaaa caaccattat tacgcaccta cattaaaaat  3804 catccaccaa agaagaaacc atcctcaaga gggttccc                          3842

<210> SEQ ID NO 8
<211> LENGTH: 198
<212> TYPE: PRT
<213> ORGANISM: Arabidopsis thaliana

<400> SEQUENCE: 8

Met Glu Asn Gly Met Tyr Lys Lys Gly Val Cys Asp Ser Cys Val
  1               5                  10                  15

Ser Ser Lys Ser Arg Ser Asn His Ser Pro Lys Arg Ser Met Met Glu
                 20                  25                  30

Pro Gln Pro His His Leu Leu Met Asp Trp Asn Lys Ala Asn Asp Leu
             35                  40                  45

Leu Thr Gln Glu His Ala Ala Phe Leu Asn Asp Pro His His Leu Met
         50                  55                  60

Leu Asp Pro Pro Glu Thr Leu Ile His Leu Asp Glu Asp Glu
 65                  70                  75                  80

Tyr Asp Glu Asp Met Asp Ala Met Lys Glu Met Gln Tyr Met Ile Ala
                 85                  90                  95

Val Met Gln Pro Val Asp Ile Asp Pro Ala Thr Val Pro Lys Pro Asn
            100                 105                 110

Arg Arg Asn Val Arg Ile Ser Asp Asp Pro Gln Thr Val Val Ala Arg
        115                 120                 125

Arg Arg Arg Glu Arg Ile Ser Glu Lys Ile Arg Ile Leu Lys Arg Ile
    130                 135                 140

Val Pro Gly Gly Ala Lys Met Asp Thr Ala Ser Met Leu Asp Glu Ala
145                 150                 155                 160

Ile Arg Tyr Thr Lys Phe Leu Lys Arg Gln Val Arg Ile Leu Gln Pro
                165                 170                 175

His Ser Gln Ile Gly Ala Pro Met Ala Asn Pro Ser Tyr Leu Cys Tyr
            180                 185                 190

Tyr His Asn Ser Gln Pro
        195

<210> SEQ ID NO 9
<211> LENGTH: 27
<212> TYPE: DNA
<213> ORGANISM: Unknown
<220> FEATURE:
```

```
<223> OTHER INFORMATION: Description of Unknown Organism:Unknown

<400> SEQUENCE: 9
ccgtcgacga tgggaagagg tagggtt                                27

<210> SEQ ID NO 10
<211> LENGTH: 20
<212> TYPE: DNA
<213> ORGANISM: Unknown
<220> FEATURE:
<223> OTHER INFORMATION: Description of Unknown Organism:Unknown

<400> SEQUENCE: 10
aatcattacc aagatatgaa                                        20

<210> SEQ ID NO 11
<211> LENGTH: 18
<212> TYPE: DNA
<213> ORGANISM: Unknown
<220> FEATURE:
<223> OTHER INFORMATION: Description of Unknown Organism:Unknown

<400> SEQUENCE: 11
cggatagctc gaatatcg                                          18

<210> SEQ ID NO 12
<211> LENGTH: 18
<212> TYPE: DNA
<213> ORGANISM: Unknown
<220> FEATURE:
<223> OTHER INFORMATION: Description of Unknown Organism:Unknown

<400> SEQUENCE: 12
aaccattgcg tcgtttgc                                          18

<210> SEQ ID NO 13
<211> LENGTH: 24
<212> TYPE: DNA
<213> ORGANISM: Unknown
<220> FEATURE:
<223> OTHER INFORMATION: Description of Unknown Organism:Unknown

<400> SEQUENCE: 13
gtaattacca ggcaaggact ctcc                                   24

<210> SEQ ID NO 14
<211> LENGTH: 24
<212> TYPE: DNA
<213> ORGANISM: Unknown
<220> FEATURE:
<223> OTHER INFORMATION: Description of Unknown Organism:Unknown

<400> SEQUENCE: 14
gtcatcggcg ggggtcataa cgtg                                   24

<210> SEQ ID NO 15
<211> LENGTH: 24
<212> TYPE: DNA
<213> ORGANISM: Unknown
<220> FEATURE:
<223> OTHER INFORMATION: Description of Unknown Organism:Unknown

<400> SEQUENCE: 15
gaggatagag aacactacga atcg                                   24
```

```
<210> SEQ ID NO 16
<211> LENGTH: 20
<212> TYPE: DNA
<213> ORGANISM: Unknown
<220> FEATURE:
<223> OTHER INFORMATION: Description of Unknown Organism:Unknown

<400> SEQUENCE: 16
caggtcaagt caatagattc                                              20

<210> SEQ ID NO 17
<211> LENGTH: 22
<212> TYPE: DNA
<213> ORGANISM: Unknown
<220> FEATURE:
<223> OTHER INFORMATION: Description of Unknown Organism:Unknown

<400> SEQUENCE: 17
cagaatttag tgaataatat tg                                           22

<210> SEQ ID NO 18
<211> LENGTH: 26
<212> TYPE: DNA
<213> ORGANISM: Unknown
<220> FEATURE:
<223> OTHER INFORMATION: Description of Unknown Organism:Unknown

<400> SEQUENCE: 18
ggagatctga attcatcttc ccatcc                                       26

<210> SEQ ID NO 19
<211> LENGTH: 65
<212> TYPE: DNA
<213> ORGANISM: Unknown
<220> FEATURE:
<223> OTHER INFORMATION: Description of Unknown Organism:Unknown

<400> SEQUENCE: 19
ccggtacctc aaacaagttg cagaggtggt tggtcttggt tggaggaatt ctgattcggt  60
tcaag                                                              65

<210> SEQ ID NO 20
<211> LENGTH: 21
<212> TYPE: DNA
<213> ORGANISM: Unknown
<220> FEATURE:
<223> OTHER INFORMATION: Description of Unknown Organism:Unknown

<400> SEQUENCE: 20
gaaggtggga gtagtcacga c                                            21

<210> SEQ ID NO 21
<211> LENGTH: 20
<212> TYPE: DNA
<213> ORGANISM: Unknown
<220> FEATURE:
<223> OTHER INFORMATION: Description of Unknown Organism:Unknown

<400> SEQUENCE: 21
cggaaggagg gttgacggca                                              20

<210> SEQ ID NO 22
<211> LENGTH: 21
<212> TYPE: DNA
<213> ORGANISM: Unknown
<220> FEATURE:
```

-continued

```
<223> OTHER INFORMATION: Description of Unknown Organism:Unknown

<400> SEQUENCE: 22
ggtggtgcga gtaatgaagt a                                              21

<210> SEQ ID NO 23
<211> LENGTH: 20
<212> TYPE: DNA
<213> ORGANISM: Unknown
<220> FEATURE:
<223> OTHER INFORMATION: Description of Unknown Organism:Unknown

<400> SEQUENCE: 23
tggtcggagg gttaacggcg                                                20
```

REDUCTION OF LIGNIN BIOSYNTHESIS IN TRANSGENIC PLANTS

This application is based on, and claims the benefit of U.S. Provisional Application No. 60/090,649, filed Jun. 25, 1998, which is herein incorporated by reference.

BACKGROUND OF THE INVENTION

1. Field of the Invention

The present invention relates generally to agriculture and plant genetic engineering and more specifically to the production of genetically modified vascular plants in which the natural process of lignification is reduced or enhanced.

2. Background Information

Plant cell wall lignins (from the Latin lignum: wood) occur exclusively in higher plants and represent the second most abundant organic compound on the earth's surface after cellulose, accounting for about 25% of plant biomass. Cell wall lignification involves the deposition of phenolic polymers (lignins) on the extracellular polysaccharide matrix. The polymers arise from the oxidative coupling of three cinnamyl alcohols. The main function of lignins is to strengthen the plant vascular body, and the rigidity and structural support provided by lignification are thought to have had an important role in the successful land colonization of plants. In addition, lignins provide mechanical support for stems and leaf blades as well as resistance to diseases, insects, cold temperatures and other biotic and abiotic stresses. Thus, lignification can be a beneficial process.

Although lignins are essential for competitive survival of vascular plants, their resistance to degradation has had a negative impact on certain agricultural and industrial uses of plants. Animals lack the enzymes for degrading the polysaccharides in cell walls and depend on microbial fermentation to break down plant fibers. High lignin concentration and methoxyl content reduce the digestibility of forage crops, such as alfalfa, by cattle, with cattle able to digest only 40–50% of legume fibers and 60–70% of grass fibers. Lignins are believed to limit forage digestibility by interfering with microbial degradation of fiber polysaccharides. However, small decreases in lignin content are predicted to have a significant positive impact on forage digestibility.

High lignin content also is problematic in the wood products industries, which contribute about 4% of the US Gross National Product and are an important component of the global economy. In wood-pulp and paper industries, lignins are undesirable components that must be removed by costly chemical pulping. Most of the lignin found in the space between the fibers and in the secondary wall is removed during the pulping and bleaching process. The chemical treatments necessary to remove lignins generate pollutants. Thus, both the digestibility of forage crops and the pulping properties of trees are adversely effected by high lignin content.

Genetic engineering has great promise for agriculture because it can accelerate traditional breeding programs, cross reproductive barriers and introduce specific, desired traits. Genetic engineering can be particularly advantageous to forestry because traditional methods are hampered by the long generation times of trees. Yet, previous attempts to generate transgenic plants with altered lignin content have targeted biosynthetic enzymes and resulted in undesirable pleiotropic effects.

Thus, there is a need for identifying genes that specifically regulate the lignification process and for methods of genetically modifying cultivated vascular plants to reduce their lignin content. Such methods would allow the more efficient use of plant biomass in animal husbandry where lignin-containing grass and legume crops are used as forage and in the pulp and paper industries. The present invention satisfies this need and provides related advantages as well.

SUMMARY OF THE INVENTION

The present invention provides a method of reducing lignification in a vascular plant by ectopically expressing a nucleic acid molecule encoding an AGL8-like gene product, whereby lignification is reduced due to ectopic expression of the nucleic acid molecule. In a method of the invention, the AGL8-like gene product can have substantially the amino acid sequence of an AGL8 ortholog and can be, for example, Arabidopsis AGL8 (SEQ ID NO:2). The methods of the invention can be particularly useful for reducing lignification in woody plants such as Eucalyptus, leguminous forage crops such as alfalfa, and in forage grasses.

In one embodiment, the invention provides a method of reducing lignification by introducing into a vascular plant an exogenous nucleic acid molecule encoding an AGL8-like gene product to produce a transgenic vascular plant characterized by reduced lignification. In such a method, the exogenous nucleic acid molecule encoding an AGL8-like gene product can be operatively linked to an exogenous regulatory element that is a constitutive regulatory element or to a tissue-selective regulatory element, for example, an AGL1 regulatory element, an AGL5 regulatory element, or a lignified tissue-selective regulatory element such as a fiber-selective regulatory element, xylem-selective regulatory element or tracheid selective regulatory element.

The invention also provides a method of reducing lignification in a vascular plant. The method includes the step of suppressing both AGL1 and AGL5 expression in the vascular plant, whereby lignification is reduced.

Further provided by the invention is a transgenic vascular plant characterized by reduced lignification, which contains an ectopically expressed nucleic acid molecule including a lignified tissue-selective regulatory element operatively linked to a nucleic acid molecule encoding an AGL8-like gene product. The AGL8-like gene product can have, for example, substantially the amino acid sequence of an AGL8 ortholog and can be, for example, Arabidopsis AGL8 (SEQ ID NO: 2). In a transgenic vascular plant of the invention characterized by reduced lignification, the lignified tissue-selective regulatory element can be, for example, a fiber-selective regulatory element, xylem-selective regulatory element or tracheid selective regulatory element. Tissues derived from a transgenic vascular plant characterized by reduced lignification also are provided herein.

The invention also provides a method of enhancing lignification in a vascular plant by ectopically expressing a nucleic acid molecule encoding an AGL1/5-like gene product, whereby lignification is enhanced due to ectopic expression of the nucleic acid molecule. In a method of the invention for enhancing lignification, the AGL1/5-like gene product can have substantially the amino acid sequence of an AGL1 ortholog and can be, for example, Arabidopsis AGL1 (SEQ ID NO:4). An AGL1/5-like gene product also can have, for example, substantially the amino acid sequence of an AGL5 ortholog and can be, for example, Arabidopsis AGL5 (SEQ ID NO: 6). The methods of the invention can be particularly valuable for enhancing lignification in woody plants or trees that are produced for direct utilization as fuel.

In one embodiment, the invention provides a method of enhancing lignification in a vascular plant by introducing an exogenous nucleic acid molecule encoding an AGL1/5-like gene product into the vascular plant to produce a transgenic vascular plant characterized by enhanced lignification. The exogenous nucleic acid molecule encoding an AGL1/5-like gene product can be operatively linked to an exogenous regulatory element, which can be a constitutive regulatory element or tissue-selective regulatory element. An AGL1/5-like gene product useful in the invention can have substantially the amino acid sequence of an AGL1 ortholog such as Arabidopsis AGL1 (SEQ ID NO:4), or can have substantially the amino acid sequence of an AGL5 ortholog such as Arabidopsis AGL5 (SEQ ID NO:6).

The invention additionally provides methods of enhancing lignification in a vascular plant by suppressing AGL8-like gene product expression in the vascular plant, whereby lignification is enhanced.

Further provided by the invention is a transgenic vascular plant characterized by enhanced lignification, comprising an ectopically expressed nucleic acid molecule comprising a lignified tissue-selective regulatory element operatively linked to a nucleic acid molecule encoding an AGL1/5-like gene product. In a transgenic vascular plant of the invention characterized by enhanced lignification, the AGL1/5-like gene product can have substantially the amino acid sequence of an AGL1 ortholog such as Arabidopsis AGL1 (SEQ ID NO:4), or substantially the amino acid sequence of an AGL5 ortholog such as Arabidopsis AGL5 (SEQ ID NO:6), and the lignified tissue-selective regulatory element can be, for example, a fiber-selective regulatory element, xylem-selective regulatory element or a tracheid selective regulatory element. Tissues derived from a transgenic vascular plant of the invention characterized by enhanced lignification also are provided.

The invention also provides kits for producing a transgenic vascular plant characterized by altered lignification. Such kits contain a nucleic acid molecule including a lignified tissue-selective regulatory element and a nucleic acid molecule encoding an AGL8-like gene product, AGL1-like gene product or AGL5-like gene product. Lignified tissue-selective regulatory elements useful in a kit of the invention include xylem-selective regulatory elements, tracheid-selective regulatory elements, and fiber-selective regulatory elements.

The invention also provides methods of enhancing lignification in a vascular plant by ectopically expressing a nucleic acid molecule encoding an R-like bHLH gene product in the vascular plant, where lignification is enhanced due to ectopic expression of the nucleic acid molecule. In a method of the invention, the R-like bHLH gene product can have substantially the amino acid sequence of an R-like bHLH ortholog such as SEQ ID NO:25. Such methods can be particularly useful for enhancing lignification in woody plants such as trees produced for direct utilization as fuel.

In one embodiment, the invention provides a method of enhancing lignification by introducing an exogenous nucleic acid molecule encoding a R-like bHLH gene product into a vascular plant to produce a transgenic vascular plant characterized by enhanced lignification. The exogenous nucleic acid molecule encoding a R-like bHLH gene product can be operatively linked to an exogenous regulatory element such as a constitutive regulatory element or tissue-selective regulatory element.

The invention also provides a transgenic vascular plant characterized by enhanced lignification, which contains an ectopically expressed nucleic acid molecule including a heterologous regulatory element operatively linked to a nucleic acid molecule encoding a R-like bHLH gene product. The encoded R-like bHLH gene product can have substantially the amino acid sequence of a R-like bHLH ortholog such as the Arabidopsis ortholog SEQ ID NO:25.

The invention further provides a method of reducing lignification in a vascular plant by suppressing R-like bHLH expression in said vascular plant, whereby lignification is reduced. In addition, the invention provides a non-naturally occurring vascular plant characterized by reduced lignification, in which R-like bHLH expression in suppressed, whereby lignification is reduced. In one embodiment, the non-naturally occurring vascular plant does not have suppressed R-like bHLH expression due to ectopic expression of AGL8 or due to suppressed AGL1 and AGL5 expression.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7 shows the nucleotide (SEQ ID NO:1) and amino acid (SEQ ID NO:2) sequence of Arabidopsis AGL8.

FIG. 8 shows the nucleotide sequence (SEQ ID NO:24) and amino acid (SEQ ID NO:25) of Arabidopsis R-like basic helix-loop-helix transcription factor (R-like bHLH). The nucleotide sequence SEQ ID NO:24 includes sufficient promoter sequence to give valve margin specific expression.

DETAILED DESCRIPTION OF THE INVENTION

Figure 1:
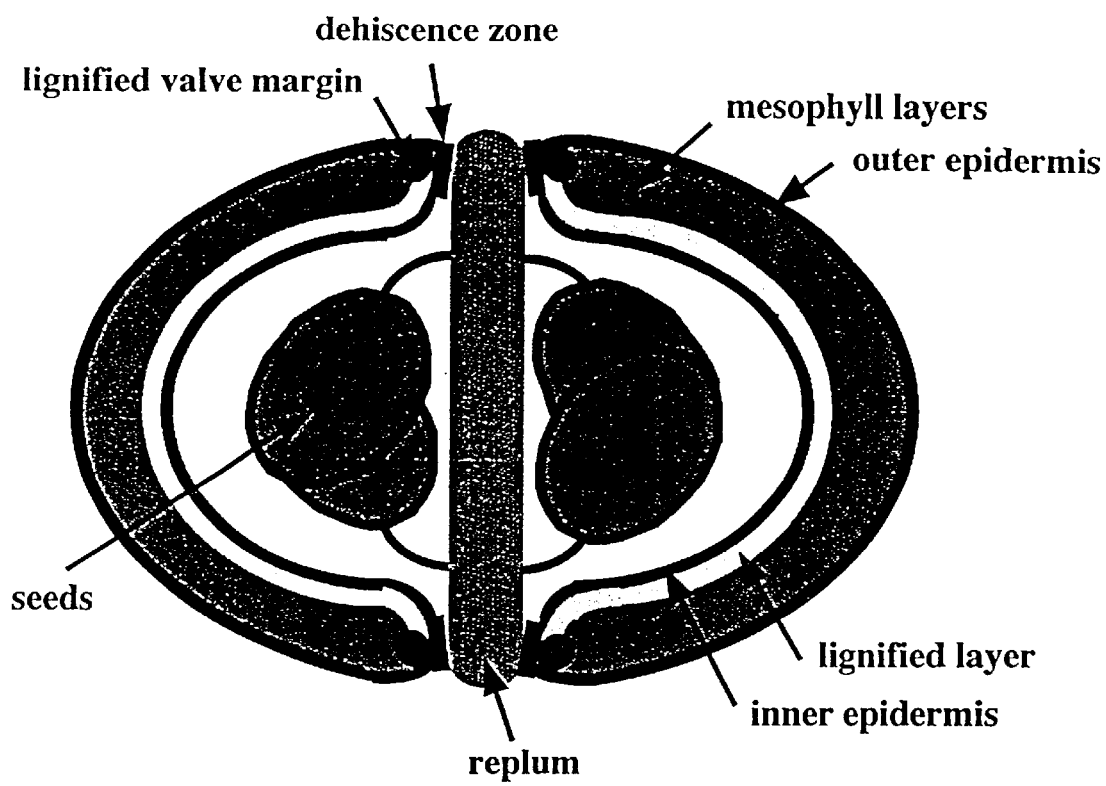
FIG. 1 shows the cell types of the Arabidopsis fruit at maturity. Indicated are the two lignified cell types: the lignified valve margin and the lignified fifth valve layer ("lignified layer").
Figure 2:
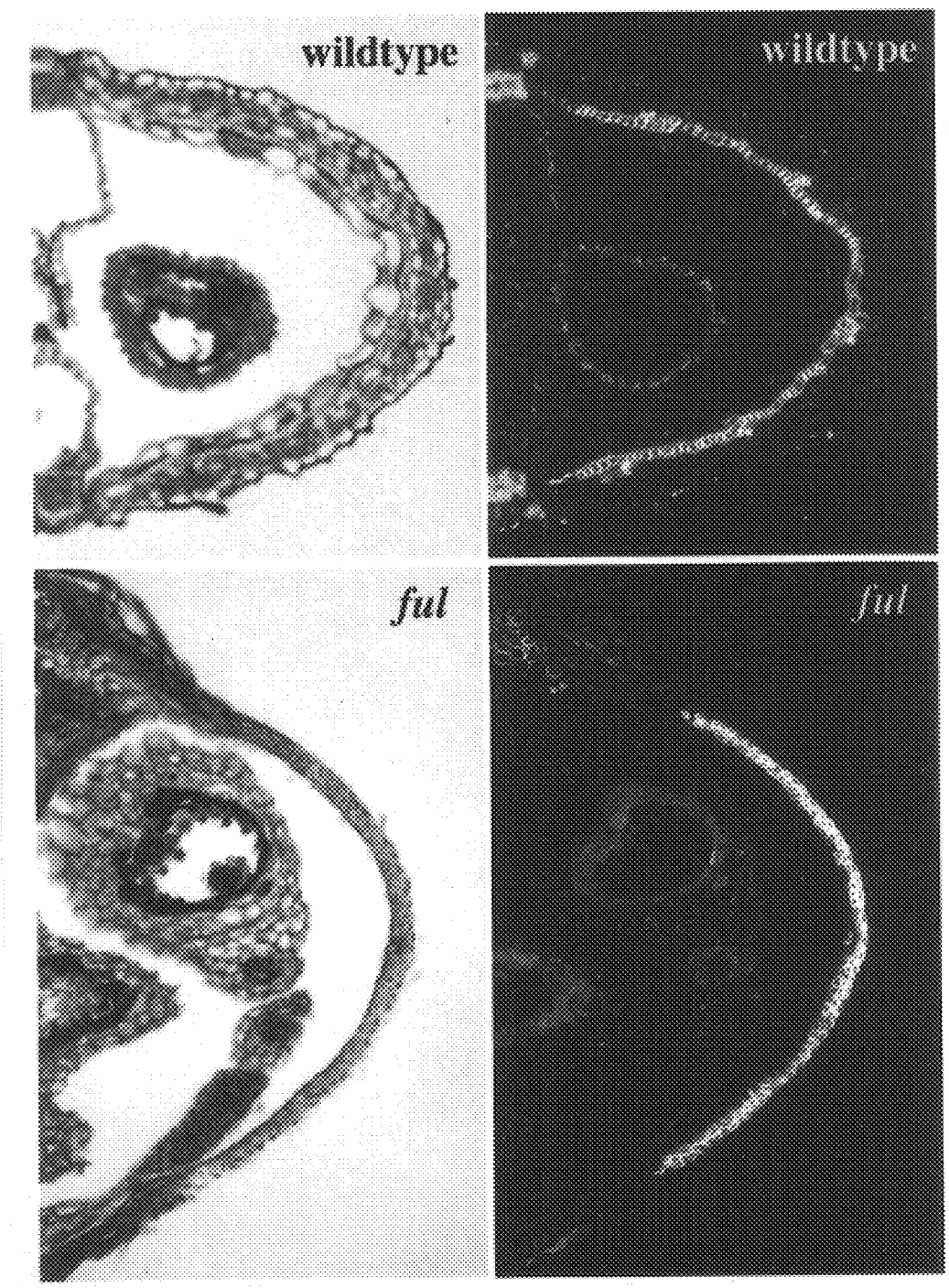
FIG. 2 shows characterization of the lignification pattern of wild-type and agl8 ("ful") fruits. Transverse sections of wild-type and agl8 fruits (stage 17) were stained with toluidine blue and viewed with Nomarski optics. Bright field (A,C) and dark field photographs (B,D) are shown of the same wild type (A,B) and agl8 (C,D) sections. The staining and autofluorescence patterns of lignified cells differ between wild-type (A,B) and agl8 (C,D) sections. Whereas wild-type sections show patches of lignified cells adjacent to the valve margin, and lignification of the fifth valve cell layer, agl8 sections show lignification of additional valve cell layers corresponding to mesophyll layers. Lignification of the fifth valve cell layer and of the vascular bundles in the replum appears unaffected in agl8 fruits, although the vascular bundles appear more disorganized.

The present invention is directed to the surprising discovery that the AGL8, AGL1, AGL5 and the R-like basic helix-loop-helix transcription factor (R-LIKE bHLH) regulate the process of lignification. As disclosed herein, an agl8 mutant Arabidopsis plant exhibits altered lignification properties, displaying enhanced lignification. Whereas wild type plants show patches of lignified cells adjacent to the valve margin, and lignification of the fifth valve cell layer, agl8 plants exhibit lignification of additional valve cell layers corresponding to internal mesophyll layers (see FIGS. 1 and 2). Furthermore, in a transgenic vascular plant constitutively expressing AGL8 under control of the cauliflower mosaic virus (35S CaMV) promoter, the number of lignified cells adjacent to the dehiscence zone was reduced. These results indicate that, in nature, the AGL8 transcription factor is a negative regulator of lignification.

Figure 3:
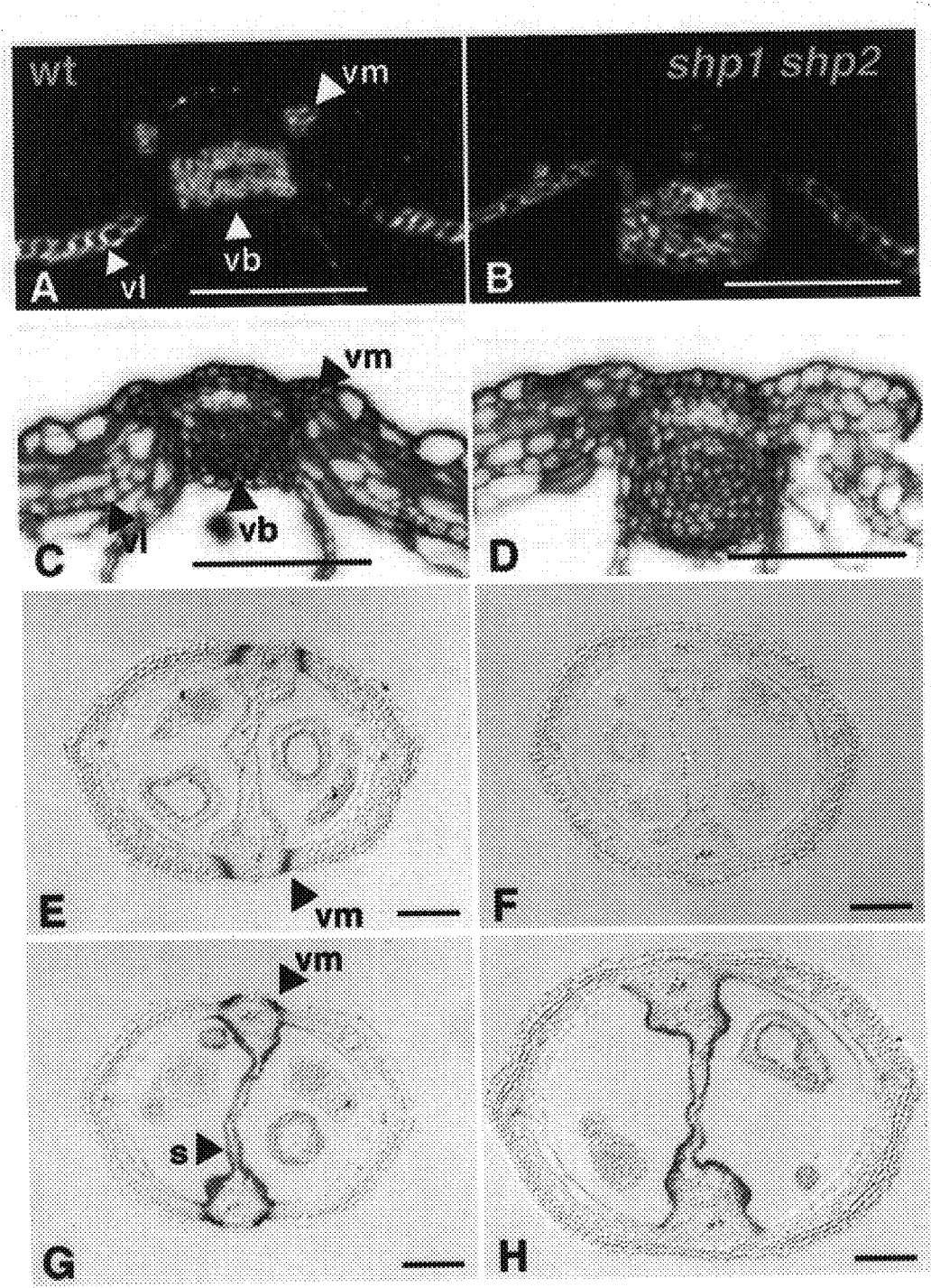
FIGS. 3.(A–H) shows histological and molecular characterization of wild-type ("wt") and agl1 agl5 ("shp1 shp2") fruits. (A–D) Transverse sections of wild type and agl1 agl5 fruits (stage 17) were stained with toluidine blue and viewed with Nomarski optics. Dark field (A,B) and bright-field photographs (C,D) are shown of the same wild type (A,C) and agl1 agl5 (B,D) sections. The autofluorescence pattern of lignified cells differs between wild-type and agl1 agl5 sections at the valve margin. Whereas both wild-type and agl1 agl5 sections exhibit lignification of the vascular bundles (vb) at either ends of the replum and of the fifth valve cell layer (vl), in wild-type fruits small patches of valve margin (vm) cells immediately adjacent to the dehiscence zone are also lignified and these lignified cells are absent in agl1 agl5 fruits. Positions of the lignified valve margin cells, valve layer and vascular bundles are also indicated in the wild-type bright-field photograph. (E–H) Expression of valve margin molecular markers in wild-type and agl1 agl5 fruits (stage 17). Transverse sections of wild-type (E,G) and agl1 agl5 (F,H) fruits containing either the GT140 (E,F) or YJ36 (G,H) molecular markers are shown. In wild-type fruits (E), expression of the GT140 marker occurs in stripes at the valve margin (vm) and these stripes are absent in agl1 agl5 fruits (F). The YJ36 marker is expressed on the outer and inner surfaces of the valve margin in wild-type (G) but not in agl1 agl5 (H) fruits. YJ36 expression is also found within the septum (s) of both wild-type and agl1 agl5 fruits. All scale bars represent 100 um.
Figure 4:
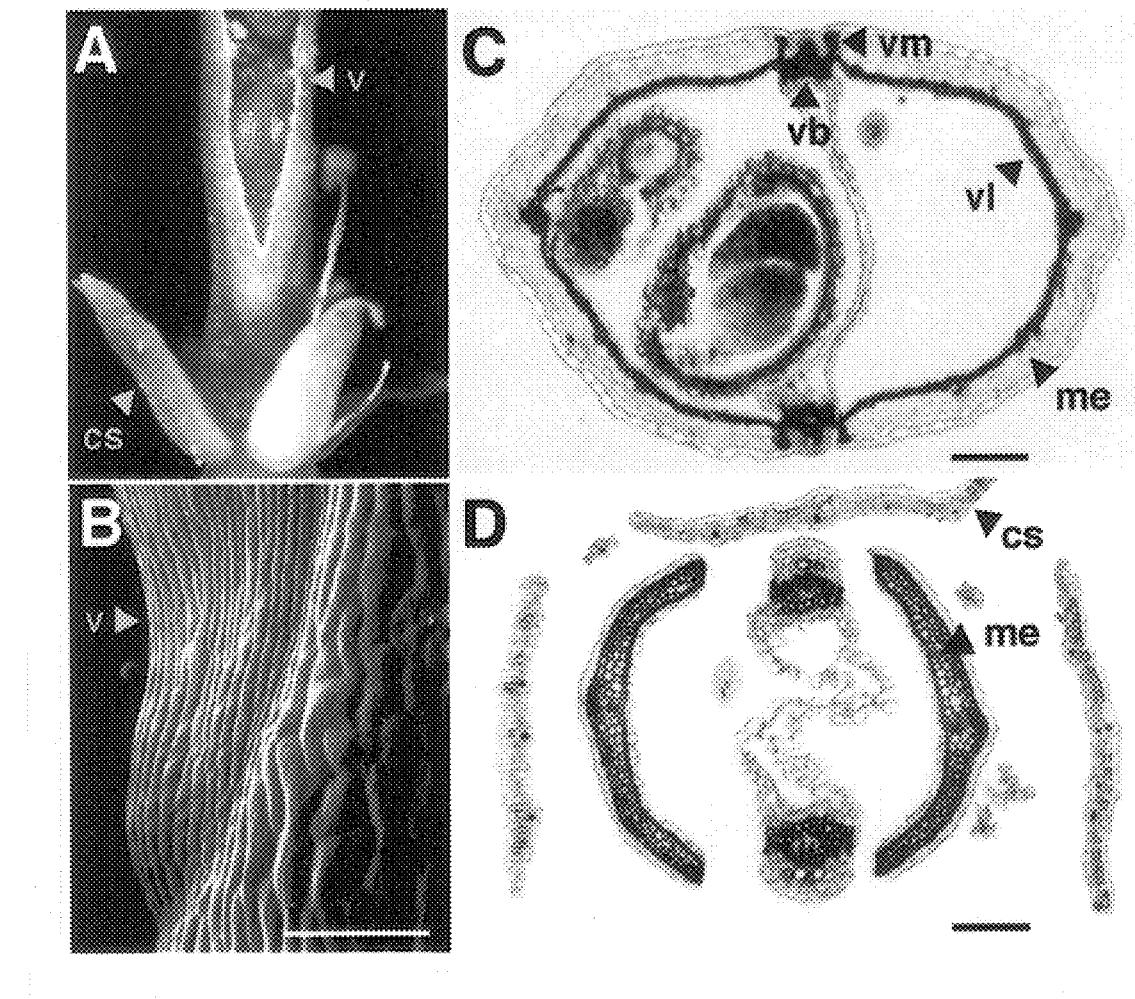
FIGS. 4(A–D) shows characterization of 35S::AGL1 35S::AGL5 fruits. (A) Photograph of 35S::AGL1 35S::AGL5 fruit near maturity (stage 17). As in agl8 fruits, the valves (v) of 35S::AGL1 35S::AGL5 fruits usually tear open due to seed crowding. (B) Scanning electron micrograph of the 35S::AGL1 35S::AGL5 fruit (stage 17). Guard cells and associated subsidiary cells are not apparent in 35S::AGL1 35S::AGL5 valves. Instead the valve epidermis consists of a homogeneous population of long, slender cells. (C,D) Transverse sections of wild-type (C) and 35S::AGL1 35S::AGL5 fruits (D) show ectopic lignification of all valve mesophyll cells (me) rather than just the valve margin (vm) cells adjacent to the dehiscence zone as found in wild-type fruits (C). Lignification of the vascular bundles (vb) and of the fifth valve layer (vi) is not affected in 35S::AGL1 35S::AGL5 fruits. Carpelloid sepals (cs) present in the outer whorl of 35S::AGL1 35S::AGL5 flowers (A,D) also show some ectopic lignification. All scale bars represent 100 $\mu$m.

As further disclosed herein, the AGL1, AGL5 and R-Like bHLH transcription factors can be positive regulators of lignification. As shown in FIG. 3, patches of lignified cells adjacent to the dehiscence zones in wild type plants were absent in fruit from an agl1 agl5 double mutant Arabidopsis plant although lignification of the fifth valve cell layer was not affected. As shown in FIG. 4, transgenic 35S::AGL1 and 35S::AGL1 35S::AGL5 Arabidopsis lines were characterized by enhanced lignification, in particular ectopic lignification of the valve mesophyll layers with the most extensive lignification apparent in 35S::AGL1 35S::AGL5 fruits.

As disclosed herein, the R-like bHLH gene product also can be a positive regulator of lignification: R-like bHLH is ectopically expressed in all valve cell layers of agl8 and 35S::AGL1 35S::AGL5 fruits, which are characterized by enhanced lignification. Furthermore, R-like bHLH was largely absent from cells at the valve margin in agl1 agl5 fruit characterized by reduced lignification. Together, the results disclosed herein indicate that the natural balance of AGL8, AGL1, AGL5, and R-like bHLH, each of which are referred to herein as a "lignification regulatory factor," can be used to reduce or enhance lignification, thereby providing improved vascular plant varieties for human use.

Thus, the present invention provides a method of reducing lignification in a vascular plant by ectopically expressing a nucleic acid molecule encoding an AGL8-like gene product, whereby lignification is reduced due to ectopic expression of the nucleic acid molecule. In a method of the invention, the AGL8-like gene product can have substantially the amino acid sequence of an AGL8 ortholog and can be, for example, Arabidopsis AGL8 (SEQ ID NO:2). The methods of the invention can be particularly useful for reducing lignification in a woody plant such as Eucalyptus, cottonwood, alder, Douglas fir, Hemlock, pine or spruce. The methods of the invention also are valuable for reducing lignification in a leguminous plant, for example, a leguminous forage crop such as alfalfa, clover, lucerne, birdsfoot trefoil, Stylosanthes, *Lotononis bainessii* or sainfoin. Similarly, the methods of the invention can be used to reduce lignification in a forage grass such as bahiagrass, bermudagrass, dallisgrass, pangolagrass, big bluestem, indiangrass, switchgrass, smooth bromegrass, orchardgrass, timothy, Kentucky bluegrass or tall fescue.

In one embodiment, the invention provides a method of reducing lignification by introducing into a vascular plant an exogenous nucleic acid molecule encoding an AGL8-like gene product to produce a transgenic vascular plant characterized by reduced lignification. In such a method, the exogenous nucleic acid molecule encoding an AGL8-like gene product can be operatively linked to an exogenous regulatory element that is a constitutive regulatory element or to a tissue-selective regulatory element, for example, an AGL1 regulatory element, an AGL5 regulatory element, or a lignified tissue-selective regulatory element such as a fiber-selective regulatory element, xylem-selective regulatory element or tracheid selective regulatory element.

Lignins represent the second most abundant organic compound on the earth's surface after cellulose and account for about 25% of the plant biomass. Lignins are typically associated with the development of the vascular system in plants. Lignins are present in a various cell types, with the greatest proportion of lignins deposited in cells walls of tracheids, vessel elements, xylem and phloem fibers, and sclereids, with the nature of the lignins differing according to cell type.

Figure 5A:
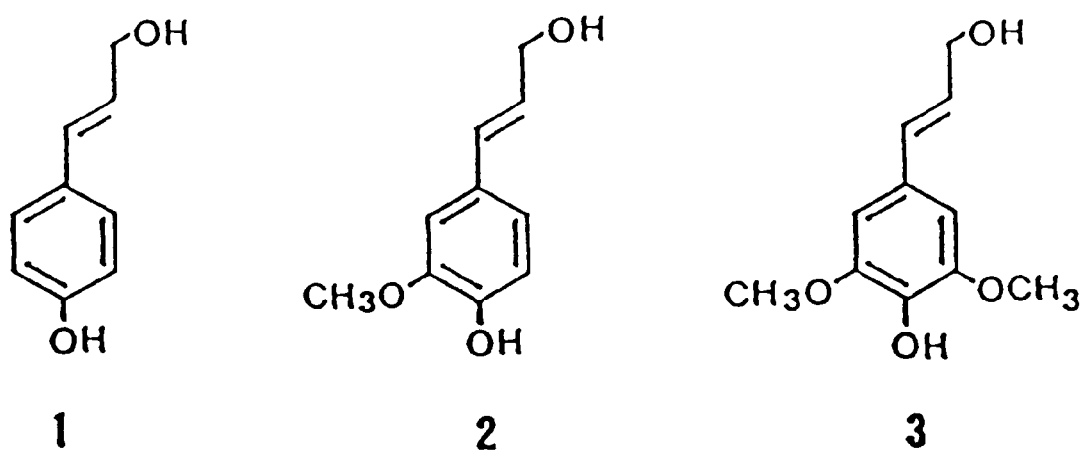
FIGS. 5(A–B) shows the three cinnamyl alcohols and their principal bonding patterns in native lignins. A. Structure of three cinnamyl alcohols. Structure of (1) p-coumaryl alcohol; (2) coniferyl alcohol; and (3) sinapyl alcohol. B. Principal bonding patterns between phenolic units in native lignins. (a) guaiacylglycerol-$\beta$-aryl ether; (b) phenylcoumaran; (c) diarylpropane; (d) resinol; (e) biphenyl; and (f) diphenyl ether. The pino-, medio-, and syringa-resinol structures involve 2G, 1G/1S, and 2S units. R is H or $OCH_3$.

Lignins are amorphous heteropolymers that are produced by the oxidative coupling of the three cinnamyl alcohols, p-coumaryl, coniferyl, and sinapyl alcohol, producing, respectively, H (hydroxyphenyl), G (guaiacyl) and S (syringyl) units in the lignin polymer (see FIG. 5A). Lignins exhibit a high degree of structural variability, which is dependent upon the species of origin and the tissue and cell types. This heterogeneity is principally reflected in the relative proportion of the three constituent monomers, the different types of interunit linkages and the occurrence of nonconventional phenolic units within the polymer (Barcelό, *International Rev. Cytology* 176:87–132 (1997), which is incorporated herein by reference). Distinctive variation in lignin content is found between the gymnosperms and angiosperms. In gymnosperms, lignins are typically composed of G units with a minor proportion of H units, while in angiosperms lignin is mainly composed of G-S units.

Figure 5B:
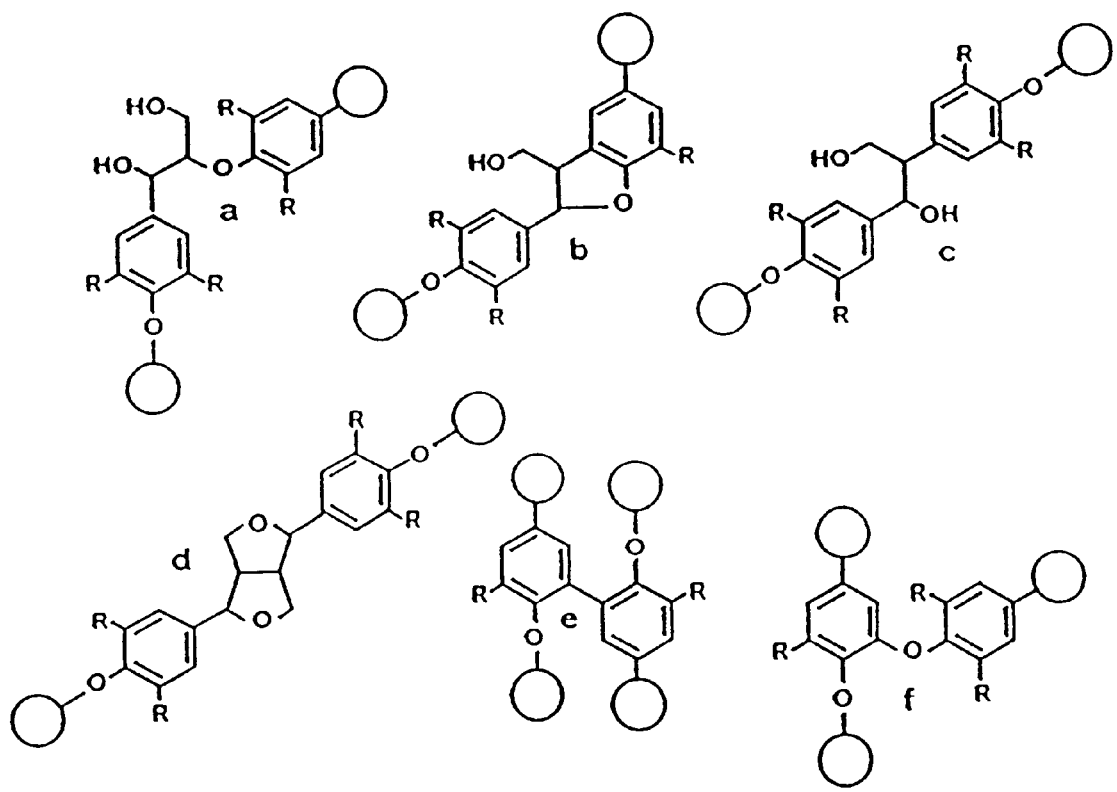

The three cinnamyl alcohols are oxidatively coupled to form a hydrophobic network of phenylpropanoid units. Phenylpropane units are interconnected in lignins by a series of ether and carbon-carbon linkages, in various bonding patterns, leading to several main substructures; quaiacylglycerol-β-aryl-ether, phenylcoumaran, diarylpropane, resinol, biphenyl, and diphenyl ether (see FIG. 5B).

The most frequent inter-unit bonds, β-O-4, are present in guaiacylglycerol-β aryl ether substructures and are the targets of most lignin depolymerization processes. In contrast, other bonds, such as β-5 (in phenylcoumaran), β-1 (in diarylpropane); β—β (in resinol), 5—5 (in biphenyl), and 5-O-4 (in diphenyl ether) interunit bonds, are very resistant to degradation. In addition to these main inter-unit linkages, there are minor ones, such as the β-6 bonds of phenylisochroman structures, or the noncyclic benzyl ether bonds, α-O-4.

Biosynthesis of lignins begins with enzymes in, the phenylpropanoid pathway, phenylalanine ammonia-lyase (PAL), cinnamate-4-hydroxyxylase (C4H), p-coumarate-3-hydroxylase (C3H), O-methyltransferase (OMT), ferulate-5-hydroxylase (F5H), and hydroxylcinnamate CoA ligase (4CL). The end products of this pathway, the hydroxycinnamoyl CoAs, are the precursors of lignins but also of other phenolic compounds that accumulate in great amounts in plant tissues such as flavanoids and tannins.

The lignin-opecific pathway involves two reductive steps that convert the hydroxycinnamoyl-CoA esters into hydroxycinnamyl alcohols. These two consecutive steps are catalyzed by the enzymes cinnamoyl-CoA reductase (CCR) and cinnamyl alcohol dehydrogenase (CAD), which are considered specific to the lignification pathway. In particular, CCR catalyzes the conversion of hydroxycinnamoyl-CoA esters to their corresponding aldehydes as the first step in the lignin-specific pathway. CAD appears as a polymorphic enzyme in angiosperms and apparently a single enzyme in gymnosperms (Lacombe et al., *The Plant J.* 11:429–441 (1997), which is incorporated by reference herein).

As used herein, the term "lignification" refers to the process giving rise to a polymer containing one or more of the H (hydroxyphenyl), G (guaiacyl) or S (syringyl) units. The H. G. and S units can be coupled by an ether, carbon-carbon, or other linkage; can be linear or branched; and can vary in the extent of their methylation. In addition, the term "lignification," as used herein, refers to the production of relatively small lignins such as lignans and neolignans, which are products that generally result from the oxidative coupling of two cinnamyl alcohols (or cinnamic acids) although other oligomeric forms can exist. Lignans are phenylpropanoid units interconnected via β—β carbon-carbon linkages and, in this bonding pattern, differ from neolignans, which are interconnected via linkages other than β—β linkages. Thus, the term "lignification" is used herein to refer to the formation of naturally occurring and non-naturally occurring lignins as well as lignans, neo-lignans and other lignin-like compounds.

The term "ectopically," as used herein in reference to expression of a nucleic acid molecule encoding a lignification regulatory factor such as an AGL8-like gene product, refers to an expression pattern that is distinct from the expression pattern in a wild type vascular plant. Thus, one skilled in the art understands that ectopic expression of a nucleic acid encoding, for example, an AGL8-like gene product can refer to expression in a cell type other than a cell type in which the nucleic acid molecule normally is expressed, or at a time other than a time at which the nucleic acid molecule normally is expressed, or at a level other than the level at which the nucleic acid molecule normally is expressed. In wild type Arabidopsis, for example, AGL8 expression is normally restricted during the later stages of floral development to the carpel valves and is not seen in the replum, which is the small strip of cells separating the carpel valves. However, under control of a constitutive promoter such as the cauliflower mosaic virus 35S promoter, AGL8 is expressed in the replum and, additionally, is expressed at higher than normal levels in other tissues such as valve margin and, thus, is ectopically expressed.

The term "reduced," as used herein in reference to lignification in a non-naturally occurring vascular plant of the invention, means a significantly decreased extent of lignification in one or more tissues as compared to the extent of lignification in a corresponding wild type vascular plant. Thus, the term "reduced" is used broadly to encompass both lignification that is significantly diminished as compared to the lignification in a wild type vascular plant as well as the absence of lignification, The term "reduced" also encompasses lignification that is significantly decreased in one or more tissues while wild type levels of lignification persist elsewhere in the vascular plant. One skilled in the art understands that the term "reduced" refers to a steady state level of lignification and encompasses both decreased synthesis and increased degradation of lignins.

It is recognized that there can be natural variation in the extent of lignification within a vascular plant species or variety. However, "reduced" lignification in a non-naturally occurring vascular plant of the invention readily can be identified by sampling a population of the non-naturally occurring vascular plants and determining that the extent of lignification is significantly decreased, on average, as compared to the normal distribution of lignification in a population of the corresponding wild type plant species or variety. Thus, production of non-naturally occurring vascular plants of the invention provides a means to skew the normal distribution of the extent of lignification.

As used herein, the term "non-naturally occurring," when used in reference to a vascular plant, means a vascular plant that has been genetically modified by man. A transgenic vascular plant of the invention, for example, is a non-naturally occurring vascular plane that contains an exogenous nucleic acid molecule encoding a lignification regulatory factor such as an AGL8-like gene product and, therefore, has been genetically modified by man. In addition, a vascular that contains a mutation in, for example, an AGL8-like gene product regulatory element or coding sequence as a result of calculated exposure to a mutagenic agent, such as a chemical mutagen, or an "insertional mutagen," such as a transposon, also is considered a non-naturally occurring plant, since it has been genetically modified by man. In contrast, a vascular plant containing only spontaneous or naturally occurring mutations is not a "non-naturally occurring vascular plant" as defined herein and, therefore, is not encompassed within the invention. One skilled in the art understands that, while a non-naturally occurring vascular plant typically has a nucleotide sequence that is altered as compared to a naturally occurring vascular plant, a non-naturally occurring vascular plant also can be genetically modified by man without altering its nucleotide sequence, for example, by modifying its methylation pattern.

The present invention relates to the use of nucleic acid molecules encoding particular "AGAMOUS-LIKE" or "AGL" gene products. AGAMOUS (AG) is a floral organ identity gene, one of a related family of transcription factors that, in various combinations, specify the identity of the floral organs: the petals, sepals, stamens and carpels (Bowman et al., *Devel.* 112:1–20 (1991); Weigel and Meyerowitz, *Cell* 78:203–209 (1994); Yanofsky, *Annual Rev. Plant Physiol. Mol. Biol.* 46:167–188 (1995)). The AGAMOUS gene product is essential for specification of carpel and stamen identity (Bowman et al., *The Plant Cell* 1:37–52 (1989); Yanofsky et al., *Nature* 346:35–39 (1990)). Related genes have recently been identified and denoted "AGAMOUS-LIKE" or "AGL" genes (Ma et al., *Genes Devel.* 5:484–495 (1991); Mandel and Yanofsky, *The Plant Cell* 7:1763–1771 (1995), which is incorporated herein by reference).

AGL8, like AGAMOUS and other AGL genes, is characterized, in part, in that it is a plant MADS box gene. The plant MADS box genes generally encode proteins of about 260 amino acids including a highly conserved MADS domain of about 56 amino acids (Piochmann and Meyerowitz, *Biol. Chem.* 378:1079–1101 (1997), which is incorporated herein by reference). The MADS domain, which was first identified in the *Arabidopsis AGAMOUS* and *Antirrhinum majus DEFICIENS* genes, is conserved among transcription factors found in humans (serum response factor; SRF) and yeast (MCM1; Norman et al., *Cell* 55:989–1003 (1988); Passmore et al., *J. Mol. Biol.* 204:593–606 (1988), and is the most highly conserved region of the MADS domain proteins. The MADS domain is the major determinant of sequence specific DNA-binding activity and can also perform dimerization and other accessory functions (Huang et al., *The Plant Cell* 8:81–94 (1996)). The MADS domain frequently resides at the N-terminus, although some proteins contain additional residues N-terminal to the MADS domain.

The "intervening domain" or "I-domain," located immediately C-terminal to the MADS domain, is a weakly conserved domain having a variable length of approximately 30 amino acids (Purugganan et al., *Genetics* 140:345–356 (1995)). In some proteins, the I-domain plays a role in the formation of DNA-binding dimers. A third domain present in plant MADS domain proteins is a moderately conserved 70 amino acid region denoted the "keratin-like domain" or "K-domain." Named for its similarity to regions of the keratin molecule, the structure of the K-domain appears capable of forming amphipathic helices and may mediate protein-protein interactions (Ma et al., *Genes Devel.* 5:484–495 (1991)). The most variable domain, both in sequence and in length, is the carboxy-terminal or "C-domain" of the MADS domain proteins. Dispensable for DNA binding and protein dimerization in some MADS domain proteins, the function of this C-domain remains unknown.

Arabidopsis AGL8 is a 242 amino acid MADS box protein (see FIG. 7; SEQ ID NO:2; Mandel and Yanofsky, supra, 1995). The AGL8 MADS domain resides at amino acids 2 to 56 of SEQ ID NO:2. The K-domain of AGL8 resides at amino acids 92 to 158 of SEQ ID NO:2.

In wild-type Arabidopsis, AGL8 RNA accumulates in two distinct phases, the first occurring during inflorescence development in the stem and cauline leaves and the second in the later stages of flower development (Mandel and Yanofsky, supra, 1995). In particular, AGL8 RNA is first detected in the inflorescence meristem as soon as the plant switches from vegetative to reproductive development. As the inflorescence stem elongates, AGL8 RNA accumulates in the inflorescence meristem and in the stem. Secondly, although AGL8 is not detected in the initial stages (1 and 2) of flower development, AGL8 expression resumes at approximately stage 3 in the center of the floral dome in the region corresponding to the fourth (carpel) whorl. AGL8 expression is excluded from all other primordia and the pedicel. The time of AGL8 expression in the fourth carpel whorl generally corresponds to the time at which the organ identity genes APETALA3, PISTILLATA AND AGAMOUS begin to be expressed (Yanofsky et al., *Nature* 346:35–39 (1990); Drews et al., *Cell* 65:991–1002 (1991); Jack et al., *Cell* 68:683–697 (1992); Goto and Meyerowitz, *Genes Devel.* 8:1548–1560 (1994)). At later stages, AGL8 expression becomes localized to the carpel walls, in the region that constitutes the valves of the ovary, and is absent from nearly all other cell types of the carpel. No AGL8 RNA expression is detected in the ovules, stigmatic tissues or the septum that divides the ovary. Thus, in nature, AGL8 expression during the later stages of floral development is restricted to the valves of the carpels and to the cells within the style.

As used herein, the term "AGL8-like gene product" means a gene product that has the same or similar function as Arabidopsis AGL8 such that, when ectopically expressed in a vascular plant, normal development is altered, and the extent of lignification is reduced. Arabidopsis AGL8 (SEQ ID NO:2) is an example of an AGL8-like gene product as defined herein. An AGLB-like gene product also can be characterized, in part, by its ability to interact with AGL1 and, additionally, its ability to interact with AGL5.

An AGL8-like gene product generally is characterized, in part, by having an amino acid sequence that has at least about 50% amino acid identity with the amino acid sequence of Arabidopsis AGL8 (SEQ ID NO: 2). An AGL8-like gene product can have, for example, an amino acid sequence with greater than about 65% amino acid sequence identity with Arabidopsis AGL8 (SEQ ID NO:2), preferably greater than about 75% amino acid identity with Arabidopois AGL8 (SEQ ID NO:2), more preferably greater than about 85% amino acid identity with Arabidopsis AGL8 (SEQ ID NO:2), and can be a sequence having greater than about 90%, 95% or 97% amino acid identity with Arabidopsis AGL8 (SEQ ID NO:2). These and other amino acid identities can be determined, for example, with CLUSTALW using the BLOSUM 62 matrix with default parameters.

Preferably, an AGL8-like gene product is orthologous to the vascular plant species in which it is ectopically expressed. A nucleic acid molecule encoding Arabidopsis AGL8 (SEQ ID NO:2), for example, can be ectopically expressed in an Arabidopsis plant to produce a non-naturally occurring Arabidopsis variety characterized ty reduced lignification. Similarly, a nucleic acid molecule encoding Eucalyptus AGL8 can be ectopically expressed in a Eucalyptus plant to produce a non-naturally occurring Eucalyptus variety characterized by reduced lignification.

A nucleic acid molecule encoding an AGL8-like gene product also can be ectopically expressed in a heterologous vascular plant to produce a non-naturally occurring vascular plant characterized by reduced lignification. AGAMOUS-like gene products have been widely conserved throughout the plant kingdom; for example, AGMOUS has been conserved in tomato (TAG1) and maize (ZAG1), indicating that orthologs of AGAMOUS-like genes are present in most, if not all, angiosperms (Pnueli et al., *The Plant Cell* 6;163–173 (1994); Schmidt et al., *The Plant Cell* 5:729–737 (1993)). AGL8-like gene products such as AGL8 orthologs also can be conserved and can function across species boundaries to reduce lignification. Thus, ectopic expression of a nucleic acid molecule encoding Arabidopsis AGL8 (SEQ ID NO:2) in a heterologous vascular plant such as another Brassica and can alter normal development such that the extent of lignification is reduced. Furthermore, a nucleic acid molecule encoding Arabidopsis AGL8 (SEQ ID NO:2), for example, can be ectopically expresses in more distantly related heterologous vascular plants, including dicotyledonous and monocotyledonous angiosperms and gymnosperms, for example, woody plants, leguminous plants and grasses and, upon ectopic expression, can alter normal development such that lignification is reduced in the heterologous plant.

As used herein, the term "gene product" encompasses an active segment of a lignification regulatory gene product such as an AGL8-like gene product, which is a polypeptide portion of the gene product that, when ectopically expressed, alters normal development such that lignification is altered in the same manner as the full-length gene product. An active segment can be, for example, an amino terminal, internal or carboxy terminal fragment of lignification regulatory factor such an Arabidopsio AGL8 (SEQ ID NO:2) that, when ectopically expressed in a vascular plant, alters normal development such that lignification is reduced or enhanced. An active segment of a MADS-domain containing lignification regulatory factor can include, for example, the MADS domain and can have the ability to bind DNA specifically. The skilled artisan will recognize that a nucleic acid molecule encoding an active segment of a lignification regulatory factor such as an AGL8-like gene product can be useful in producing a vascular plant of the invention characterized by reduced or enhanced lignification.

An active segment of a lignification regulatory factor such as an AGL8-like gene product can be identified using, for example, histochemical tests such as the toluidine blue O test, Wiesner's test (specific for cinnamaldehyde groups), or Maule's reaction (specific for syringyl groups; Strivastava, *Tappi* 49:173–183 (1966), which is incorporated by reference herein), or cytochemical probes such as the stain with $KMnO_4$ and Coppick and Fowler's reaction (Czaninski et al., *Biol. Cell.* 35: 97–102 (1979); Barceló, supra, 1997, each of which is incorporated by reference herein). Quantitative determination of lignins also can be achieved by various direct and indirect methods, including direct chemical methods such as the preparation of "Klason lignins" and "thioglycolate lignins" (Effland, *Tappi* 60:143–144 (1977), which is incorporated by reference herein). Spectrophotometric methods, including the acetyl-bromide method consisting of the solubilization of lignins with acetyl bromide in glacial acetic acid, can be used with lignified tissues that do not contain significant amounts of ester-bound cinnamic acids (Johnson et al., *Tappi* 44:793–798 (1961); Iiyama and Wallis, *Wood Sci. Technol.* 22:271–280 (1988), each of which is incorporated herein by reference). Additional in situ microscopic techniques include UV microscopy based on the blue autofluorescence of lignins illuminated with UV light (Scott et al., *Wood Sci. Technol.* 3:73–92 (1969), which is incorporated herein by reference), interference microscopy (Donaldson, *N.Z. J. For, Sci.* 15:349–360 (1985), which is incorporated herein by reference); and bromination in conjunction with energy-dispersive X-ray analysis (Saka et al., *Tappi* 61:73–76 (1978), which is incorporated herein by reference). If desired, the nature and monomer composition of lignins also can be determined by routine chemical and physical methods (Bartelo, supra, 1997).

A vascular plant such as Arabidopsis can be transformed with a nucleic acid molecule under control of a constitutive regulatory element such as a tandem CaMV 35S promoter. Microscopic analysis of toluidine blue sections from transgenic and wild type vascular plants reveals whether a plant ectopically expressing a particular polypeptide portion is characterized by reduced lignification. For analysis of a large number of polypeptide portions of a lignification regulatory gene product, nucleic acid molecules encoding the polypeptide portions can be assayed in pools, and active pools subsequently subdivided to identify the active nucleic acid molecule.

In one embodiment, the invention provides a non-naturally occurring plant that is characterized by reduced lignification due to ectopic expression of a nucleic acid molecule encoding an AGL8-like gene product having substantially the amino acid sequence of an AGL8 ortholog. As used herein, the term "AGL8 ortholog" means an ortholog of Arabidopsis AGL8 (SEQ ID NO:2) and refers to an AGL8-like gene product that, in a particular plant variety, has the highest percentage homology at the amino acid level to Arabidopsis AGL8 (SEQ ID NO:2). An AGL8 ortholog can be, for example, a Eucalyptus AGL8 ortholog or an alfalfa AGL8 ortholog. An AGL8 ortholog from the long-day plant Sinapis alba, designated SaMADS B, has been described (Menzel et al., *Plant J.* 9:399–408 (1996), which is incorporated herein by reference). Similarly, the sequence of the tomato AGL8 ortholog is available as EST244966 under accession number AI486645. Novel AGL8 ortholog cDNAs can be isolated from additional plant species using a nucleotide sequence as a probe and methods well known in the art of molecular biology (Glick and Thompson (eds.), *Methods in Plant Molecular Biology and Biotechnology*, Boca Raton, Fla.: CRC Press (1993); Sambrook et al. (eds.), *Molecular Cloning: A Laboratory Manual* (Second Edition), Plainview, N.Y.: Cold Spring Harbor Laboratory Press (1989), each of which is incorporated herein by references.

As used herein, the term "substantially the amino acid sequence," when used in reference to an AGL8 ortholog or an ortholog of another lignification regulatory factor, is intended to mean a polypeptide or polypeptide segment having an identical amino acid sequence, or a polypeptide or polypeptide segment having a similar, non-identical sequence that is considered by those skilled in the art to be a functionally equivalent amino acid sequence. For example, an AGL8-like gene product having substantially the amino acid sequence of Arabidopsis AGL8 can have an amino acid sequence identical to the sequence of Arabidopsis AGL8 (SEQ ID NO;2) shown in FIG. 7, or a similar, non-identical sequence that is functionally equivalent. In particular, an amino acid sequence that is "substantially the amino acid sequence" of a lignification regulatory factor such as AGL8 can have one or more modifications such as amino acid additions, deletions or substitutions relative to the Arabidopsis amino acid sequence shown, provided that, when ectopically expressed in the vascular plant, the modified polypeptide retains substantially the ability to alter normal development such that lignification is reduced in the case of AGL8, or enhanced in the case of AGL1, AGL5 or R-like bHLH. Comparison of sequences for substantial similarity can be performed between two sequences of any length and usually is performed with sequences between about 6 and 1200 residues, preferably between about 10 and 100 residues and more preferably between about 25 and 35 residues. Such comparisons for substantial similarity are performed using methodology routine in the art.

It is understood that minor modifications of primary amino acid sequence can result in a lignification regulatory factor, such as an AGL8-like gene product, that has substantially equivalent or enhanced function as compared to the ortholog from which it was derived. Further, various molecules can be attached to an ortholog or active segment thereof, for example, other polypeptides, antigenic or other peptide tags, carbohydrates, lipids, or chemical moieties. For example, a heterologous activation domain can be fused to the full-length sequence, or substituted for the naturally occurring activation of one of the disclosed lignification regulatory factors disclosed herein. Such modifications are included within the term "ortholog" as defined herein.

One or more point mutations can be introduced into a nucleic acid molecule encoding a lignification regulatory factor to yield a modified nucleic acid molecule using, for example, site-directed mutagenesis (see Wu (Ed.), *Meth. In Enzymol.* Vol. 217, San Diego: Academic Press (1993); Higuchi, "Recombinant PCR" in Innis et al. (Ed.), *PCR Protocols,* San Diego: Academic Press, Inc. (1990), each of which is incorporated herein by reference). Such mutagenesis can be used to introduce a specific, desired amino acid insertion, deletion or substitution; alternatively, a nucleic acid sequence can be synthesized having random nucleotides at one or more predetermined positions to generate random amino acid substituting. Scanning mutagenesis also can be useful in generating a modified nucleic acid molecule encoding substantially the amino acid sequence of an ortholog such as an AGL8 ortholog. Modified nucleic acid molecules can be routinely assayed for the ability to reduce lignification using, for example, microscopic analysis of toluidine blue stained sections or another method described hereinabove.

The methods of the invention can be used to reduce or, as set forth below, enhance lignification in one of a variety of vascular plant species, including a variety of monocotyledonous and dicotyledonous angiosperms and gymnosperms. As used herein, the term "vascular plant" means a higher plant capable of producing lignins, such as an angiosperm or gymnosperm. An angiosperm is a seed-bearing plant whose seeds are borne in a mature ovary (fruit) and are divided into two broad classes based on the number of cotyledons or seed leaves that generally store or absorb food. Thus, the invention can be practiced, for example, with a monocotyledonous or dicotyledonous angiosperm, or with a gymnosperm, which is a seed-bearing plant with seeds not enclosed in an ovary.

In one embodiment, the invention provides a method of reducing lignification in a woody plant. Woody plants, including conifer and hardwood trees such as, for example, Eucalyptus, cottonwood, alder, Douglas fir, Hemlock, pine and spruce, can be modified as disclosed herein to produce a tree characterized by reduced lignification. The skilled person understands that the invention can be practiced with these or other woody plants or trees, especially trees useful for producing pulp or paper (Whetten and Sederoff, *Forest Ecology and Management* 43:301–316 (1991), which is incorporated herein by reference).

In another embodiment, the invention provides a method of reducing lignification in a leguminous plant. A leguminous plant can produce a forage legume, such as alfalfa, lucerne, birdsfoot trefoil, clover, Stylosanthes species, *Lotononis bainessii* or sainfoin (Buxton and Redfearn, *J. Nutr.* 127:814S–818S (1997); Dixon et al., *Gene* 179:61–71 (1996), each of which is incorporated herein by reference). The skilled artisan will recognize that these or other leguminous plants can be modified as disclosed herein to produce a non-naturally occurring plant variety characterized by reduced lignification.

In another embodiment, the invention provides a method of reducing lignification in a forage grass, such forage grasses useful as they are more easily digestible by cattle. The methods of the invention can be used, for example, to reduce lignification in a forage grass such as bahiagrass, bermudagrass, dallisgrass, pangolagrasg, big bluestem, indiangrass, switchgrass, smooth bromegrass, orchardgrass, timothy, Kentucky bluegrass or tall fescue.

The term "exogenous," as used herein in reference to a nucleic acid molecule and a transgenic vascular plant, means a nucleic acid molecule originating from outside the vascular plant. An exogenous nucleic acid molecule can be, for example, a nucleic acid molecule encoding an AGL8-like gene product or an exogenous regulatory element such as a constitutive or tissue-selective regulatory element. An exogenous nucleic acid molecule can have a naturally occurring or non-naturally occurring nucleotide sequence and can be a heterologous nucleic acid molecule derived from a different species than the plant into which the nucleic acid molecule is introduced or can be a nucleic acid molecule derived from the same plant species as the plant into which it is introduced.

The term "operatively linked," as used in reference to a regulatory element and a nucleic acid molecule, means that the regulatory element confers regulated expression upon the operatively linked nucleic acid molecule. Thus, the term "operatively linked," as used in reference to an exogenous regulatory element such as a constitutive regulatory element and a nucleic acid molecule encoding a lignification regulatory factor such as an AGL8-like gene product, means that the constitutive regulatory element is linked to the nucleic acid molecule encoding an AGL8-like gene product such that a constitutive expression pattern is conferred upon the nucleic acid molecule encoding the AGL8-like gene product. It is recognized that a regulatory element and a nucleic acid molecule that are operatively linked have, at a minimum, all elements essential for transcription, including, for example, a TATA box.

As used herein, the term "constitutive regulatory element" means a regulatory element that confers a level of expression upon an operatively linked nucleic molecule that is relatively independent of the cell or tissue type in which the constitutive regulatory element is expressed. A constitutive regulatory element that is expressed in a vascular plant generally is widely expressed in a large number of cell and tissue types.

A variety of constitutive regulatory elements useful for ectopic expression in a transgenic vascular plant are well known in the art. The cauliflower mosaic virus 35S (CaMV 35S) promoter, for example, is a well-characterized constitutive regulatory element that produces a high level of expression in all plant tissues (Odell et al., *Nature* 311:810–812 (1985)). The CaMV 35S promoter can be particularly useful due to its activity in numerous diverse plant species (Benfey and Chua, *Science* 250:959–966 (1990); Futterer et al., *Physiol.*

Plant 79:154 (1990); Odell et al., supra, 1985). A tandem 35S promoter, in which the intrinsic promoter element has been duplicated, Confers higher expression levels in comparison to the unmodified 35S promoter (Kay et al., *Science* 236:1299 (1987)). Other constitutive regulatory elements useful for ectopically expressing a nucleic acid molecule encoding an AGL8-like gene product in a transgenic vascular plant of the invention include, for example, the cauliflower mosaic virus 19S promoter; the Figwort mosaic virus promoter; and the nopaline synthase (nos) gene promoter (Singer et al., *Plant Mol. Biol.* 14:433 (1990); An, *Plant Physiol.* 81:86 (1986)).

Additional constitutive regulatory elements including those for efficient ectopic expression in monocots also are known in the art, for example, the pEmu promoter and promoters based on the rice Actin-1 5' region (Last et al., *Theor. Appl. Genet.* 81:581 (1991); Mcelroy et al., *Mol. Gen. Genet.* 231:150 (1991); Mcelroy et al., *Plant Cell* 2:163 (1990)). Chimeric regulatory elements, which combine elements from different genes, also can be useful for ectopically expressing a nucleic acid molecule encoding an AGL8-like gene product (Comai et al., *Plant Mol. Biol.* 15:373 (1990)). One skilled in the art understands that a particular constitutive regulatory element is chosen based, in part, on the plant species in which a nucleic acid molecule encoding an AGL8-like gene product is to be ectopically expressed and on the desired level of expression.

An exogenous regulatory element useful in a transgenic vascular plant of the invention also can be an inducible regulatory element, which is a regulatory element that confers conditional expression upon an operatively linked nucleic acid molecule, where expression of the operatively linked nucleic acid molecule is increased in the presence of a particular inducing agent or stimulus as compared to expression of the nucleic acid molecule in the absence of the inducing agent or stimulus. Particularly useful inducible regulatory elements include copper-inducible regulatory elements (Mett et al., *Proc. Natl. Acad. Sci. USA* 90:4567–4571 (1993); Furst et al., *Cell* 55:705–717 (1988)); tetracycline and chlor-tetracycline-inducible regulatory elements (Gatz et al., *Plant J.* 2:397–404 (1992); Röder et al., *Mol. Gen. Genet.* 243:32–38 (1994); Gatz, *Meth. Cell Biol.* 50:411–424 (1995)); ecdysone inducible regulatory elements (Christopherson et al., *Proc, Natl. Acad. Sci. USA* 89:6314–6318 (1992); Kreutzweiser et al., *Ecotoxicol. Environ. Safety* 28:14–24 (1994)), heat shock inducible regulatory elements (Takahashi et al., *Plant Physiol.* 99:383–390 (1992); Yabe et al., *Plant Cell Physiol.* 35:1207–1219 (1994); Ueda et al., *Mol. Gen. Genet.* 250:533–539 (1996)); and lac operon elements, which are used in combination with a constitutively expressed lac repressor to confer, for example, IPTG-inducible expression (Wilde et al., *EMBO J.* 11:1251–1259 (1992)).

An inducible regulatory element useful in the transgenic vascular plants of the invention also can be, for example, a nitrate-inducible promoter derived from the spinach nitrite reductase gene (Back et al., *Plant Mol. Biol.* 17:9 (1991)) or a light-inducible promoter, such as that associated with the small subunit of RuBP carboxylase or the LHCP gene families (Feinbaum et al., *Mol. Gen. Genet.* 226:449 (1991); Lam and Chua, *Science* 248:471 (1990)). Additional inducible regulatory elements include salicylic acid inducible regulatory elements (Uknes et al., *Plant Cell* 5:159–169 (1993); Bi et al., *Plant J.* 8:235–245 (1995)); plant hormone-inducible regulatory elements (Yamaguchi-Shinozaki et al., *Plant Mol. Biol.* 15:905 (1990); Kares et al., *Plant Mol. Biol.* 15:225 (1990)); and human hormone-inducible regulatory elements such as the human glucocorticoid response element (Schena et al., *Proc. Natl. Acad. Sci. USA* 88:10421 (1991)).

Tissue-selective regulatory elements also can be useful in the invention. Such a tissue-selective regulatory element, which can be used to ectopically express a nucleic acid molecule in a single tissue or in a limited number of tissues, can be, for example, a xylem-selective regulatory element, a tracheid-selective regulatory element or a fiber-selective regulatory element. Such tissue-selective regulatory elements are known in the art or can be isolated using routine methodology (Glick and Thompson, supra, 1993).

A dehiscence zone-selective regulatory element also can be a tissue-selective regulatory element useful in the invention. A dehiscence zone-selective regulatory element can be derived from AGL1 or AGL5 or a gene that is an ortholog of Arabidopsis AGL1 or AGL5 and is selectively expressed in the valve margin or dehiscence zone of a vascular plant. Dehiscence zone-selective regulatory elements also can be derived from a variety of other genes that are selectively expressed in the valve margin or dehiscence zone of a vascular plant. For example, the rapeseed gene RDPG1 is selectively expressed in the dehiscence zone (Petersen et al., *Plant Mol. Biol.* 31:517–527 (1996), which is incorporated herein by reference). Thus, the RDPG1 promoter or an active fragment thereof can be a dehiscence zone-selective regulatory element as defined herein. Additional genes such as the rapeseed gene SAC51 also are known to be selectively expressed in the dehiscence zone; the SAC51 promoter or an active fragment thereof also can be a dehiscence zone-selective regulatory element of the invention (Coupe et al., *Plant Mol, Biol.* 23:1223–1232 (1993), which is incorporated herein by reference). Further, genes selectively expressed in the dehiscence zone include the R-like bHLU gene that confers selective GUS expression in the Arabidopsis transposant line GT140 (Sundaresan et al., *Genes Devel.* 9:1797–1810 (1995), which is incorporated herein by reference).

Transgenic vascular plants characterized by reduced lignification also are provided by the invention. Such transgenic plants contain an ectopically expressed nucleic acid molecule including a lignified tissue-selective regulatory element operatively linked to a nucleic acid molecule encoding an AGL8-like gene product. The AGL8-like gene product can have, for example, substantially the amino acid sequence of an AGL8 ortholog and can be, for example, Arabidopsis AGL8 (SEQ ID NO: 2). In a transgenic vascular plant of the invention characterized by reduced lignification, the lignified tissue-selective regulatory element can be, for example, a fiber-selective regulatory element, xylem-selective regulatory element or tracheid selective regulatory element.

Further provided herein is a tissue derived from a transgenic vascular plant containing an ectopically expressed nucleic acid molecule that contains a lignified tissue-selective regulatory element operatively linked to a nucleic acid molecule encoding an ACL8-like gene product.

As used herein, the term "transgenic" refers to a vascular plant that contains an exogenous nucleic acid molecule, which can be derived from the same plant species or a heterologous plant species.

As used herein, the term "lignified tissue-selective regulatory element" refers to a nucleotide sequence that, when operatively linked to a nucleic acid molecule, confers selective expression upon the operatively linked nucleic acid molecule in a limited number of vascular plant tissues, including one or more lignified tissues such as fiber, xylem or tracheid tissue. One skilled in the art understands that a lignified tissue-selective regulatory element can confer specific expression exclusively in cells that normally are lignified in a wild type vascular plant or can confer selective expression in a limited number of plant cell types including lignified cells.

Lignified tissue-selective regulatory elements are known in the art, for example, a useful xylem-selective regulatory element can be a phenylalanine ammonia-lyase (PAL) promoter sequence. Poplar PAL1 or PAL2 promoter sequences, for example, can be used to direct xylem-selective expression in heterologous transgenic plants, for example, in developing primary xylem of leaves, stems and other organs and in secondary xylem of stems (Gray-Mitsumune et al., *Plant Mol. Biol.* 39:657–659 (1999); accession number AF038863 and AF038864).

It should be recognized that a non-naturally occurring vascular plant of the invention, which contains an ectopically expressed nucleic acid molecule encoding an AGL8-like gene product, also can contain one or more additional modifications, including naturally and non-naturally occurring modifications, that can modulate the reduction in lignification or provide other advantageous properties. Such vascular plants are encompassed within the invention.

The methods of the invention entail ectopically expressing a nucleic acid molecule encoding a lignification regulatory factor to alter the natural lignification process. In one embodiment, the methods include introducing an ectopically expressible nucleic acid molecule encoding an AGL8-like gene product into the vascular plant, whereby lignification is reduced due to ectopic expression of the nucleic acid molecule.

As discussed above, the term "ectopically" refers to expression of a nucleic acid molecule encoding a lignification regulatory factor in a cell type other than a cell type in which the nucleic acid molecule is normally expressed, at a time other than a time at which the nucleic acid molecule is normally expressed or at an expression level other than the level at which the nucleic acid normally is expressed. In wild type Arabidopsis, for example, AGL8 expression is normally restricted during the later stages of floral development to the carpel valves. In the methods of the invention, particularly useful ectopic expression of a nucleic acid molecule encoding an AGL8-like gene product involves expression in cell types that in wild type plants can be lignified, for example, within the stem or xylem, leaves, or fruit, such as adjacent to the dehiscence zone.

Actual ectopic expression of lignification regulatory factor is dependent on various factors. The ectopic expression can be widespread expression throughout most or all plant tissues or can be expression restricted to a small number of plant tissues, and can be achieved by a variety of routine techniques. Mutagenesis, including seed or pollen mutagenesis, can be used to generate a non-naturally occurring vascular plant, in which a nucleic acid molecule encoding a lignification regulatory factor, for example, an AGL8-like gene product is ectopically expressed. Ethylmethane sulfonate (EMS) mutagenesis, transposon mediated mutagenesis or T-DNA mediated mutagenesis also can be useful in ectopically expressing a lignification regulatory factor to produce a vascular plant characterized by reduced or enhanced lignification (see, generally, Glick and Thompson, supra, 1993). While not wishing to be bound by any particular mechanism, ectopic expression in a mutagenized plant can result from inactivation of one or more negative regulators of a lignification regulatory factor, for example, ectopic expression of AGL8 can result from the combined inactivation of AGL1 and AGL5.

Ectopic expression of a lignification regulatory factor such as an AGL8-like gene product also can be achieved by expression of a nucleic acid encoding the regulatory factor from a heterologous regulatory element or from a modified variant of its own promoter. Heterologous regulatory elements include constitutive regulatory elements, which result in expression of the lignification regulatory factor in most or all plant cell types, and tissue-selective regulatory elements, which produce selective expression of the lignification regulatory factor in a limited number of cell types.

Ectopic expression of a nucleic acid molecule encoding a lignification regulatory factor such as an AGL8-like gene product can be achieved using an endogenous or exogenous nucleic acid molecule encoding the regulatory factor. A recombinant exogenous nucleic acid molecule can contain a heterologous regulatory element that is operatively linked to a nucleic acid sequence encoding the lignification regulatory factor. Methods for producing the desired recombinant nucleic acid molecule under control of a heterologous regulatory element and for producing a non-naturally occurring vascular plant of the invention are well known in the art (see, generally, Sambrook et al., supra, 1989; Glick and Thompson, supra, 1993).

An exogenous nucleic acid molecule can be introduced into a vascular plant for ectopic expression using a variety of transformation methodologies including Agrobacterium-mediated transformation and direct gene transfer methods such as electroporation and microprojectile-mediated transformation (see, generally, Wang et al. (eds), *Transformation of Plants and Soil Microorganisms,* Cambridge, UK: University Press (1995), which is incorporated herein by reference). Transformation methods based Upon the soil bacterium Agrobacterium tumefaciens are particularly useful for introducing an exogenous nucleic acid molecule into a vascular plant. The wild type form of Agrobacterium contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An Agrobacterium-based vector is a modified form of a Ti plasmid, in Which the tumor inducing functions are replaced by the nucleic acid sequence of interest to be introduced into the plant host.

Agrobacterium-mediated transformation generally employs cointegrate vectors or, preferably, binary vector systems, in which the components of the Ti plasmid are divided between a helper vector, which resides permanently in the Agrobacterium host and carries the virulence genes, and a shuttle vector, which contains the gene of interest bounded by T-DNA sequences. A variety of binary vectors are well known in the art and are commercially available, for example, from Clontech (Palo Alto, Calif.). Methods of coculturing Agrobacterium with cultured plant cells or wounded tissue such as leaf tissue, root explants, hypocotyledons, stem pieces or tubers, for example, also are well known in the art (Glick and Thompson, supra, 1993). Wounded cells within the plant tissue that have been infected by Agrobacterium can develop organs de novo when cultured under the appropriate conditions; the resulting transgenic shoots eventually give rise to transgenic plants that ectopically express a nucleic acid molecule encoding an AGL8-like gene product. Agrobacterium also can be used for transformation of whole plants as described in Bechtold et al., *C.R. Acad, Sci. Paris. Life Sci.* 316:1194–1199 (1993), which is incorporated herein by reference). Agrobacterium-mediated transformation is useful for producing a variety of transgenic vascular plants (Wang et al., supra, 1995) including at least one species of Eucalyptus and forage legumes such as alfalfa (lucerne); birdsfoot trefoil, white clover, Stylosanthes, *Lotononis bainessii* and sainfoin.

Microprojectile-mediated transformation also can be used to produce a transgenic vascular plant that ectopically expresses a lignification regulatory factor. This method, first described by Klein et al. (*Nature* 327:70–73 (1987), which is incorporated herein by reference), relies on microprojectiles such as gold or tungsten that are coated with the desired nucleic acid molecule by precipitation with calcium chloride, spermidine or PEG. The microprojectile particles are accelerated at high speed into an angiosperm tissue using a device such as the BIOLISTIC PD-1000 (Biorad; Hercules Calif.).

Microprojectile-mediated delivery or "particle bombardment" is especially useful to transform plants that are difficult to transform or regenerate using other methods. Microprojectile-mediated transformation has been used, for example, to generate a variety of transgenic vascular plant speciesr including cotton, tobacco, corn, hybrid poplar and papaya (see Glick and Thompson, supra, 1993) as well as cereal crops such as wheat, oat, barley, sorghum and rice (Duan et al., *Nature Biotech.* 14:494–498 (1996); Shimamoto, *Curr. Opin. Biotech.* 5:158–162 (1994), each of which is incorporated herein by reference). In view of the above, the skilled artisan will recognize that Agrobacterium-mediated or microprojectile-mediated transformation, as disclosed herein, or other methods known in the art can be used to introduce a nucleic acid molecule encoding a lignification regulatory factor such as an AGL8-like gene product into a vascular plant for ectopic expression.

The invention also provides a method of reducing lignification in a vascular plant by suppressing both AGL1 and AGL5 expression in the vascular plant, whereby lignification is reduced.

As disclosed herein, loss-of-function mutations in the AGL1 and AGL5 genes were produced by a combination of homologous recombination and disruptive T-DNA insertion (see Example II). Neither AGL1 nor AGL5 RNA was expressed in the resulting agl1 agl5 double mutant, and toluidine blue staining and microscopy revealed that the patches of cells which normally are lignified in wild type plants are absent in the agl1 agl5 mutant. These results indicate that AGL1 or AGL5 gene expression is required for normal lignification and that suppression AGL1 expression combined with suppression of AGL5 expression in the vascular plant can reduce lignification, allowing plant varieties with improved characteristics to be developed.

The Arabidopsis AGL1 and AGL5 genes encode MADS box proteins with 85% identity at the amino acid level (see Tables 1 and 2). The AGL1 and AGL5 RNA expression patterns also are strikingly similar. In particular, both RNAs are specifically expressed in flowers, where they accumulate in developing carpels. In particular, strong expression of these genes is observed in the outer replum along the valve/replum boundary (Ma et al., supra, 1991; Savidge et al., *The Plant Cell* 7:721–723 (1995); Flanagan et al., *The Plant Journal* 10:343–353 (1996), each of which is incorporated herein by reference).

TABLE 1

Amino acid identity in the MADS domain and K-domain of AGAMOUS, AGL1 and AGL5

|  | AGAMOUS | | AGL1 | | AGL5 | |
| --- | --- | --- | --- | --- | --- | --- |
|  | MADS | K | MADS | K | MADS | K |
| AGAMOUS | — | — | 95% | 68% | 95% | 62% |
| AGL1 | — | — | — | — | 100% | 92% |
| AGL5 | — | — | — | — | — | — |

TABLE 2

Amino acid identity in the I-domain and C-domain of AGAMOUS, AGL1 and AGL5

|  | AGAMOUS | | AGL1 | | AGL5 | |
| --- | --- | --- | --- | --- | --- | --- |
|  | I | C | I | C | I | C |
| AGAMOUS | — | — | — | — | — | — |
| AGL1 | 71% | 39% | — | — | — | — |
| AGL5 | 65% | 37% | 95% | 72% | — | — |

As used herein, the term "AGL1" refers to Arabidopsis AGL1 (SEQ ID NO:4) or an ortholog of Arabidopsis AGL1 (SEQ ID NO:4). An AGL1 ortholog is a MADS box gene product characterized, in part, by positively regulating the process of lignification and, in part, by having homology to the amino acid sequence of Arabidopsis AGL1 (SEQ ID NO:4). AGL1 or an AGL1 ortholog can function, in part, by forming a complex with an AGL8-like gene product. An AGL1 ortholog generally has an amino acid sequence having at least about 63% amino acid identity with Arabidopsis AGL1 (SEQ ID MO:4) and includes polypeptides having greater than about 70%, 75%, 85% or 95% amino acid identity with Arabidopsis AGL1 (SEQ ID NO:4). Given the close relatedness of the AGL1 and AGL5 gene products, one skilled in the art will recognize that an AGL1 ortholog can be distinguished from an AGL5 ortholog by being more closely related to Arabidopsis AGL1 (SEQ ID NO:4) than to Arabidopsis AGL5 (SEQ ID NO:6). An AGL1 ortholog can function in wild type plants, like Arabidopsis AGL1, to limit the domain of AGL8-like gene product expression.

As used herein, the term "AGL5" refers to Arabidopsis AGL5 (SEQ ID NO:6) or to an ortholog of Arabidopsis AGL5 (SEQ ID NO:6). An AGL5 ortholog is a MADS box gene product characterized, in part, by positively regulating the process of lignification and, in part, by having homology to the amino acid sequence of Arabidopsis AGL5 (SEQ ID NO:6). AGL5 or an AGL5 ortholog can function, in part, by forming a complex with an AGL8-like gene product. An AGL5 ortholog generally has an amino acid sequence having at least about 60% amino acid identity with Arabidopsis AGL5 (SEQ ID NO:6) and includes polypeptides having greater than about 65%, 70%, 75%, 85% or 95% amino acid identity with Arabidopsis AGL5 (SEQ ID NO:6). Given the close relatedness of the AGL1 and AGL5 gene products, one skilled in the art will recognize that an AGL5 ortholog can be distinguished from an AGL1 ortholog by being more closely related to Arabidopsis AGL5 (SEQ ID NO:6) than to Arabidopsis AGL1 (SEQ ID NO:4). An AGL5 ortholog can function in wild type plants, like Arabidopsis AGL5, to limit the domain of AGL8-like gene product expression.

The invention further provides a method of reducing lignification in a vascular plant by suppressing R-like bHLH expression in said vascular plant, whereby lignification is reduced. In addition, the invention provides a non-naturally occurring vascular plant characterized by reduced lignification, in which R-like bHLH expression in suppressed, whereby lignification is reduced. In one embodiment, the non-naturally occurring vascular plant does not have suppressed R-like bHLH expression due to ectopic expression of AGL8 or due to suppressed AGL1 and AGL5 expression.

As used herein, the term "R-like bHLH gene product" means a gene product that has the same or similar function as Arabidopsis R-like bHLH such that, when ectopically expressed in a vascular plant, normal development is altered, and the extent of lignification is enhanced. Thus, a R-like bHLH gene product is characterized, in part, in that it is a positive regulator of lignification.

A R-like bHLH gene product generally is characterized, in part, by having an amino acid sequence that has at least about 50% amino acid identity with the amino acid sequence of Arabidopsis R-like bHLH (SEQ ID NO: 25). A R-like bHLH gene product can have, for example, an amino acid sequence with greater than about 65% amino acid sequence identity with Arabidopsis R-like bHLH (SEQ ID NO:25), preferably greater than about 75% amino acid identity with SEQ ID NO:25, more preferably greater than about 85% amino acid identity with SEQ ID NO:25, and can be a sequence having greater than about 90%, 95% or 97% amino acid identity with SEQ ID NO:25.

The term "suppressed," as used herein in reference to AGL1 expression, means that the amount of functional AGL1 protein is reduced in a plant in comparison with the amount of functional AGL1 protein in the corresponding wild type plant. Similarly, when used in reference to AGL5 expression, the term suppressed means that the amount of functional AGL5 protein is reduced in a plant in comparison with the amount of functional AGL5 protein in the corresponding wild type plant. When used in reference to R-like bHLH expression, the term "suppressed" means that the amount of functional R-like bHLH protein is reduced in a plant in comparison with the amount of functional R-like bHLH protein in the corresponding wild type plant. Thus, the term "suppressed," as used herein, encompasses the absence of AGL1, AGL5 or R-like bHLH protein in a plant, as well as protein expression that is present but reduced as compared to the level of expression of the corresponding protein in a wild type plant. Furthermore, the term "suppressed" refers to AGL1, AGL5 or R-like bHLH protein expression that is reduced throughout the entire domain of AGL1, AGL5 or R-like bHLH expression, or to expression that is reduced in some part of the AGL1, AGL5 or R-like bHLH expression domain, provided that the resulting plant is characterized by reduced lignification.

As used herein, the term "suppressed" also encompasses an amount of AGL1, AGL5 or R-like bHLH protein that is equivalent to wild type AGL1, AGL5 or R-like bHLH expression, but where the AGL1, AGL5 or R-like bHLH protein has a reduced level of activity. For example, AGL1 and AGL5 each contain a conserved MADS domain; point mutations or gross deletions within the MADS domain that reduce the DNA-binding activity of AGL1 or AGL5 can reduce or destroy the activity of AGL1 or AGL5 and, therefore, "suppress" AGL1 or AGL5 expression as defined herein.

A variety of methodologies can be used to Suppress AGL1, AGL5 or R-like bHLH expression in a vascular plant. Suppression can be achieved by directly modifying the AGL1, AGL5 or R-like bHLH genomic locus, for example, by modifying a regulatory sequence such that transcription or translation from the AGL1, AGL5 or R-like bHLH locus is reduced, or by modifying an AGL1, AGL5 or R-like bHLH coding sequence such that non-functional protein is produced. Suppression of AGL1, AGL5 or R-like bHLH expression in a vascular plant also can be achieved indirectly, for example, by modifying the expression or activity of a protein that regulates AGL1, AGL5 or R-like bHLH expression. Methodologies for effecting suppression of protein expression in a plant include, for example, homologous recombination, chemical and transposon-mediated mutagenesis, cosuppression and antisense-based techniques and dominant negative methodologies.

Homologous recombination can be used to suppress expression in a vascular plant as described in Kempin et al., Nature 389:802–803 (1997), which is incorporated herein by reference. Homologous recombination can be used, for example, to replace the wild type AGL5 genomic sequence with a construct in which the gene for kanamycin resistance is flanked by at least about 1 kb of AGL5 sequence. The use of homologous recombination to suppress AGL5 expression is set forth in Example II.

Suppression of AGL1, AGL5 or R-like bHLH expression also can be achieved by producing a loss-of-function mutation using transposon-mediated insertional mutagenesis with Ds transposons or Stm transposons (see, for example, Sundaresan et al., Genes Devel. 9:1797–1810 (1995), which is incorporated herein by reference). Insertion of a transposon into an AGL1, AGL5 or R-like bHLH target gene can be identified, for example, by restriction mapping, which can identify the presence of an insertion in the gene promoter or in the coding region, such that expression of functional gene product is suppressed. Insertion of a transposon also can be identified by detecting an absence of the mRNA encoded by the target gene or by the detecting the absence of the gene product in valve margin. Suppression of AGL1, AGL5 or R-like bHLH expression also can be achieved by producing a loss-of-function mutation using T-DNA-mediated insertional mutagenesis (see Krysan et al., Proc. Natl. Acad. Sci. USA 93:8145–8150 (1996)). The use of T-DNA-mediated insertional mutagenesis to suppress AGL1 expression is disclosed in Example II.

Suppression Of AGL1, AGL5 or R-like bHLH expression in a vascular plant also can be achieved using cosuppression, which is a well known methodology that relies on expression of a nucleic acid molecule in the sense orientation to produce coordinate silencing of the introduced nucleic acid molecule and the homologous endogenous gene (see, for example, Flavell, Proc. Natl. Acad. Sci., USA 91:3490–3496 (1994); Kooter and Mol, Current Opin. Biol. 4:166–171 (1993), each of which is incorporated herein by reference). Cosuppression is induced most strongly by a large number of transgene copies or by overexpression of transgene RNA and can be enhanced by modification of the transgene such that it fails to be translated.

Antisense nucleic acid molecules encoding AGL1, AGL5 or R-like bHLH gene products, or fragments thereof, also can be used to suppress expression of the corresponding gene product in a vascular plant. Antisense nucleic acid molecules reduce mRNA translation or increase mRNA degradation, thereby suppressing gene expression (see, for example, Kooter and Mol, supra, 1993; Pnueli et al., The Plant Cell Vol. 6, 175–186 (1994), which is incorporated herein by reference).

To suppress both AGL1 and AGL5 expression or R-like bHLH expression, the one or more sense or antisense nucleic acid molecules can be expressed under control of a strong regulatory element. The constitutive CaMV 35S promoter (Odell et al., supra, 1985), for example, or other constitutive promoters as disclosed herein, can be useful in the methods of the invention. Tissue-selective regulatory elements also can be useful for expressing one or more sense or antisense nucleic acid molecules in order to suppress AGL1 and AGL5, or R-like bHLH expression, in a vascular plant.

The skilled artisan will recognize that effective suppression of endogenous AGL1, AGL5 or R-like bHLH gene expression depends upon the one or more introduced nucleic acid molecules having a high percentage of homology with the corresponding endogenous gene loci. Nucleic acid molecules encoding Arabidopsis AGL1 (SEQ ID NO:3), Arabidopsis AGL5 (SEQ ID NO:5) and Arabidopsis R-like bHLH (SEQ ID No:24) are provided herein (see, also, Ma et al., supra, 1991). Nucleic acid molecules encoding Arabidopsis AGL1, AGL5 and R-like bHLH can be useful in the methods of the invention or for isolating orthologous sequences.

The homology requirement for effective suppression using homologous recombination, cosuppression or antisense methodology can be determined empirically. In general, a minimum of about 80–90% nucleic acid sequence identity is preferred for effective suppression of AGL1, AGL5 or R-like bHLH expression. Thus, a nucleic acid molecule encoding a gene ortholog from the family or genus of the plant species into which the nucleic acid molecule is to be introduced is preferred for generating the non-naturally occurring vascular plants of the invention using homologous recombination, cosuppression or antisense technology. More preferably, a nucleic acid molecule encoding a gene ortholog from the same plant species is used for suppression in a vascular plant of the invention.

Although use of a highly homologous nucleic acid molecule is preferred in the methods of the invention, the nucleic acid molecule to be used for homologous recombination, cosuppression or antisense suppression need not contain in its entirety the sequence to be suppressed. Thus, a sense or antisense nucleic acid molecule encoding only a portion of Arabidopsis AGL1 (SEQ ID NO:3), for example, or a sense or antisense nucleic acid molecule encoding only a portion of Arabidopsis AGL5 (SEQ ID NO:5), or a sense or antisense nucleic acid molecule encoding only a portion of Arabidopsis R-like bHLH (SEQ ID NO:24), can be useful for producing a non-naturally occurring vascular plant of the invention, in which AGL1 and AGL5 expression each are suppressed or in which R-like bHLH expression is suppressed.

A portion of a nucleic acid molecule to be homologously recombined with a genomic locus generally contains at least about 1 kb of sequence homologous to the targeted gene and preferably contains at least about 2 kb, more preferably at least about 3 kb and can contain at least about 5 kb of sequence homologous to the targeted gene. For example, a portion of a nucleic acid molecule encoding an AGL1 or AGL5 to be used for cosuppression or antisense suppression generally contains at least about 50 base pairs to the full-length of the nucleic acid molecule encoding the AGL1 or AGL5 ortholog. In Contrast to an active segment, as defined herein, a portion of a nucleic acid molecule to be used for homologous recombination, cosuppression or antisense suppression need not encode a functional part of a gene product.

A dominant negative construct also can be used to suppress AGL1, AGL5 or R-like bHLH expression in a vascular plant. A dominant negative construct useful in the invention generally contains a portion of the complete AGL1, AGL5 or R-like bHLH coding sequence sufficienti for example, for DNA-binding or for a protein-protein interaction such an a homodimeric or heterodimeric protein-protein interaction but lacking the transcriptional activity of the wild type protein. For example, a carboxy-terminal deletion mutant of AGAMOUS was used as a dominant negative construct to suppress expression of the MADS box gene AGAMOUS (Mizukami et al., *Plant Cell* 8:831–844 (1996), which is incorporated by reference herein). One skilled in the art understands that, similarly, a dominant negative AGL1, AGL5 or R-like bHLH construct can be used to suppress AGL1, AGL5 or R-like bHLH expression in a plant. A useful AGL1 or AGL5 dominant negative construct can be a deletion mutant encoding, for example, the MADS box domain alone ("M"), the MADS box domain and "intervening" region ("MI"); the MADS box, "intervening" and "K" domains ("MIK"); or the "intervening," "K" and carboxy-terminal domains ("IKC"), The methods of the invention for reducing lignification by suppressing both AGL1 and AGL5 expression encompass introducing a loss-of-function mutation at the AGL1 locus and a loss-of-function mutation at the AGL5 locus. Loss-of-function mutations encompass point mutations, including substitutions, deletions and insertions, as well as gross modifications of an AGL1 and AGL5 locus and can be located in coding or non-coding sequences. One skilled in the art understands that any such loss-of-function mutation at the AGL1 locus can be combined with any such mutation at the AGL5 locus to generate an agl1 agl5 double mutant of the invention. Production of an exemplary agl1 agl5 double mutant in the Brassica plant Arabidopsis is disclosed herein in Example II.

AGL1 and AGL5 are closely related genes that have diverged relatively recently. While not wishing to be bound by the following, some plants can contain only AGL1 or only AGL5, or can contain a single ancestral gene related to AGL1 and AGL5. In such plants, reduced lignificatlon can be produced by suppressing only expression of AGL1, or expression only of AGL5, or expression of a single ancestral gene related to AGL1 and AGL5. Thus, the present invention provides a non-naturally occurring vascular plant characterized by reduced lignification, in which AGL1 expression is suppressed, for example, an agl1 single mutant. The present invention also provides a non-naturally occurring vascular plant characterized by reduced lignification, in which AGL5 expression is suppressed, for example, an agl5 single mutant.

The present invention further provides a tissue derived from a non-naturally occurring vascular plant of the invention characterized by reduced lignification. In one embodiment, the invention provides a tissue derived from a non-naturally occurring vascular plant that is characterized by reduced lignification due to ectopic expression of a nucleic acid molecule encoding an AGL8-like gene product. In another embodiment, the invention provides a tissue derived from a non-naturally occurring vascular plant characterized by reduced lignification, in which AGL1 expression and AGL5 expression both are suppressed.

As used herein, the term "tissue" means an aggregate of plant cells and intercellular material organized into a structural and functional unit. A particular useful tissue of the invention is a tissue that can be vegetatively or non-vegetatively propagated such that the vascular plant from which the tissue was derived is reproduced. A tissue of the invention can be, for example, a stem, leaf, fruit or part thereof.

Based on identification of AGL1, AGL5, AGL8 and R-like bHLH as regulators of lignification, the invention also provides methods of enhancing lignification in a vascular plant. As disclosed herein, transgenic plants constitutively expressing AGL1 or AGL5 exhibit enhanced lignification, as indicated by ectopic lignification of the valve mesophyll layers revealed by staining with toluidine blue or phloroglucinol (see Example IV). As further disclosed herein, an agl8 mutant, in which AGL8 expression is suppressed, is characterized by enhanced lignification in that all the internal mesophyll cell layers are lignified rather than the single lignified enb layer in wild type fruit (see Example III). Based on the above, the invention provides methods of enhancing lignification by altering the natural levels and expression patterns of transcription factors that regulate the lignification pathway.

Non-naturally occurring plant varieties exhibiting enhanced lignification can be desirable, for example, for improved mechanical properties such as greater wind or water resistance, or increased resistance to plant pathogens. Cereal plants, for example, can be modified as disclosed herein to produce a non-naturally occurring variety characterized by enhanced lignification. High levels of lignin in wood increase the intrinsic heat content for direct utilization as fuel. Thus, enhanced lignification can be used to produce woody plant varieties with improved properties.

Based on the above, the invention provides methods of enhancing lignification in a vascular plant by ectopically expressing a nucleic acid molecule encoding an AGL1/5-like gene product, whereby lignification is enhanced due to ectopic expression of the nucleic acid molecule. In a method of the invention for enhancing lignification, the AGL1/5-like gene product can have substantially the amino acid sequence of an AGL1 ortholog and can be, for example, Arabidopsis AGL1 (SEQ ID NO:4). An AGL1/5-like gene product also can have, for example, substantially the amino acid sequence of an AGL5 ortholog and can be, for example, Arabidopsis AGL5 (5EQ ID NO: 6). The methods of the invention can be particularly valuable for enhancing lignification in woody plants or trees that are produced for direct utilization as fuel.

In one embodiment, the invention provides a method of enhancing lignification in a vascular plant by introducing an exogenous nucleic acid molecule encoding an AGL1/5-like gene product into the vascular plant to produce a transgenic vascular plant characterized by enhanced lignification. The exogenous nucleic acid molecule encoding an AGL1/5-like gene product can be operatively linked to an exogenous regulatory element, which can be a constitutive regulatory element or tissue-selective regulatory element. Tissue-selective regulatory elements useful in producing a transgenic vascular plant characterized by enhanced lignification include an AGL1 regulatory element or AGL5 regulatory element, or a lignified tissue-selective regulatory element such as a fiber-selective regulatory element, xylem-selective regulatory element or tracheid selective regulatory element. An AGL/1/5-like gene product useful in the invention can have substantially the amino acid sequence of an AGL1 ortholog such as Arabidopsis AGL1 (SEQ ID NO:4), or can have substantially the amino acid sequence of an AGL5 ortholog such as Arabidopsis AGL5 (SEQ ID NO:6).

The invention additionally provides methods of enhancing lignification in a vascular plant by suppressing AGL8-like gene product expression in the Vascular plant, whereby lignification is enhanced.

Further provided by the invention is a transgenic vascular plant characterized by enhanced lignification, containing an ectopically expressed nucleic acid molecule including a lignified tissue-selective regulatory element operatively linked to a nucleic acid molecule encoding an AGL/1/5-like gene product. In a transgenic vascular plant of the invention characterized by enhanced lignification, the AGL1/5-like gene product can have substantially the amino acid sequence of an AGL1 ortholog such as Arabidopsis AGL1 (SEQ ID NO:4), or substantially the amino acid sequence of an AGL5 ortholog such as Arabidopsis AGL5 (SEQ ID NO:6), and the lignified tissue-selective regulatory element can be, for example, a fiber-selective regulatory element, xylem-selective regulatory element or a tracheid selective regulatory element. Tissues derived from a transgenic vascular plant of the invention characterized by enhanced lignification also are provided.

The invention also provides kits for producing a transgenic vascular plant characterized by altered lignification. Such kits contain a nucleic acid molecule including a lignified tissue-selective regulatory element and a nucleic acid molecule encoding an AGL8-like gene product, AGL1-like gene product or AGL5-like gene product. Lignified tissue-selective regulatory elements useful in a kit of the invention include xylem-selecting regulatory elements, tracheid-selective regulatory elements, and fiber-selective regulatory elements.

The term "enhanced," as used herein in reference to lignification in a non-naturally occurring vascular plant of the invention, means a significantly increased extent of lignification in one or more tissues as compared to the extent of lignification in a corresponding wild type plant. Thus, the term "enhanced" is used broadly to encompass both lignification that is significantly elevated in a tissue or region in which lignification normally occurs and the presence of lignification in a tissue or region, which, in a wild type plant, is normally not lignified. The term "enhanced" also encompasses lignification that is significantly elevated in at least one tissue, although wild type levels of lignification can be present elsewhere in the plant. One skilled in the art understands that the term "enhanced" refers to a steady state level of lignification and encompasses both increased synthesis and decreased degradation of lignins.

It is recognized that there can be natural variation in the extent of lignification within a plant species or variety. However, "enhanced" lignification in a non-naturally occurring vascular plant of the invention readily can be identified by sampling a population of the non-naturally occurring vascular plants and determining that the extent of lignification is significantly increased, on average, as compared to the normal distribution of lignification in a population of the corresponding wild type plant species or variety. Thus, production of non-naturally occurring vascular plants of the invention provides a means to skew the normal distribution of the extent of lignification such that, on average, lignification is significantly greater than in a corresponding wild type plant.

As used herein, the term "AGL1/5-like gene product" means a gene product having substantially the amino acid sequence of an AGL1 ortholog or substantially the amino acid sequence of an AGL5 ortholog or substantially the amino acid sequence of a gene that is a common ancestor of AGL1 or AGL5. An AGL1/5-like gene product is characterized in part, in that it is a positive regulator of lignification. An AGL1/5-like gene product also is characterized, in part, by having an amino acid sequence with at least about 30%, 40%, 50%, 60%, 70%, 80%, 90% or 95% amino acid identity with SEQ ID NO:4 or SEQ ID NO:6. Arabidopsis AGL1 (SEQ ID NO:3) and Arabidopsis AGL5 (SEQ ID NO:5) are examples of an AGL1/5-like gene product as defined herein.

One skilled in the art understands that ectopic expression is of a level sufficient to produce enhanced lignification. Such a level of ectopic expression is achieved through use of a strong promoter and can also be achieved, for example, by multiple transgene integrations, or through ectopic expression of distinct gene products such as an AGL1 ortholog together with an AGL5 ortholog. As disclosed in Example IV, one 35S::AGL5 transgenic line did not display enhanced lignification, while both 35S::AGL1 and 35S::AGL1 35S::AGL5 lines showed enhanced lignification with the later line showing the most dramatic lignification. The results with the 35S::ACL1 35S::AGL5 line support a role for AGL5 in enhancing lignification when expressed at sufficient levels.

In view of the results disclosed herein, one skilled in the art further understands that altering the expression of additional combinations of lignification regulatory factors can be useful in reducing or enhancing lignification as desired. For example, ectopic expression of AGL8 can be used in combination with suppression of AGL1 and AGL5 and, if desired, in combination with suppression of R-like bHLH to reduce lignification in a vascular seed plant. Similarly, ectopic expression of any combination of AGL1, AGL5 and R-like bHLH can be used to enhance lignification in a vascular seed plant, and such ectopic expression can be combined, if desired, with suppression of AGL8 expression.

Methods of producing a non-naturally occurring plant characterized by enhanced lignification also are provided herein. Such methods entail ectopically expressing a nucleic acid molecule encoding an AGL1/5-like gene product in the vascular plant, whereby lignification is enhanced due to ectopic expression of the nucleic acid molecule. In one embodiment, the method entails introducing an exogenous ectopically expressible nucleic acid molecule encoding an AGL1/5-like gene product into the vascular plant, whereby lignification is enhanced due to ectopic expression of the nucleic acid molecule.

The invention also relates to the use of R-like bHLH transcription factors such as the Arabidopsis transcription factor SEQ ID NO:25. The invention provides methods of enhancing lignification in a vascular plant by ectopically expressing a nucleic acid molecule encoding an R-like bHLH gene product in the vascular plant, where lignification is enhanced due to ectopic expression of the nucleic acid molecule. In a method of the invention, the R-like bHLH gene product can have substantially the amino acid sequence of an R-like bHLH ortholog such as SEQ ID NO:25. Such methods can be particularly useful for enhancing lignification in woody plants such as trees produced for direct utilization as fuel.

In one embodiment, the invention provides a method of enhancing lignification by introducing an exogenous nucleic acid molecule encoding a R-like bHLH gene product into a vascular plant to produce a transgenic vascular plant characterized by enhanced lignification. The exogenous nucleic acid molecule encoding a R-like bHLH gene product can be operatively linked to an exogenous regulatory element such as a constitutive regulatory element or tissue-selective regulatory element.

The invention also provides a transgenic vascular plant characterized by enhanced lignification, which contains an ectopically expressed nucleic acid molecule including a heterologous regulatory element operatively linked to a nucleic acid molecule encoding a R-like bHLH gene product. The encoded R-like bHLH gene product can have substantially the amino acid sequence of a R-like bHLH ortholog such ag the Arabidopsis ortholog SEQ ID NO:25.

In one embodiment, the invention provides methods of using a nucleic acid molecule encoding a R-like bHLH ortholog. As used herein, the term "R-like bHLH ortholog" means an ortholog of Arabidopsis R-like bHLH (SEQ ID NO:25) and refers to a R-like bHLH gene product that, in a particular plant variety, has the highest percentage homology at the amino acid level to Arabidopsis R-like bHLH (SEQ ID NO:25). Such a R-like bHLH ortholog can be, for example, a Eucalyptus ortholog or an alfalfa ortholog. Novel R-like bHLH orthologous cDNAs can be identified from databases or isolated from additional plant species using a nucleotide sequence as a probe and methods well known in the art of molecular biology as described above.

The following examples are intended to illustrate but not limit the present invention.

EXAMPLE I

Production of a 35S::AGL8 Transgenic Arabidopsis Plant Displaying Reduced Lignification This example describes methods for producing a transgenic Arabidopsis plant characterized by reduced lignification due to Constitutive AGL8 expression.

Full-length AGL8 was prepared by polymerase chain reaction amplification using primer AGL8 5-α (SEQ ID NO:9; 5'-CCGTCGACGATGGGAAGAGGTAGGGTT-3') and primer OAM14 (SEQ ID NO:10; 5'-AATCATTACCAAGATATGAA-3'), and subsequently cloned into the SalI and BamHI sites of expression vector pBIN-JIT, which was modified from pBIN19 to include the tandem CaMV 35S promoter, a polycloning site and the CaMV polyA signal. Arabidopsis was transformed using the in planta method of Agrobacterium-mediated transformation essentially as described in Bechtold et al., *C.R. Acad. Sci. Paris* 316:1194–1199 (1993), which is incorporated herein by reference. Kanamycin-resistant lines were analyzed for the presence of the 35S-AGL8 construct by PCR using a primer specific for the 35S promoter and a primer specific for the AGL8 cDNA, which produced two fragments of 850 and 550 bp in the 35S::AGL8 transgenic plants. These fragments were absent in plants that had not been transformed with the 35S-AGL8 construct.

Lignification was assayed in several 35S::AGL8 Arabidopsis lines by staining fixed fruit sections with toluidine blue as described in Drews et al., *Cell* 65:991–1002 (1991)) with minor modifications. Lignified cell autofluorescence (Barceló, supra, 1997) was examined with Nomarski optics. Additional lignin histochemical analyses were performed by staining sections for two minutes in a solution of 2% phloroglucinol in 95% ethanol with subsequent photography in 50% hydrochloric acid.

The results, as seen by toluidine blue staining, demonstrated that the number of lignified cells adjacent to the dehiscence zone was reduced in the 35S::AGL8 transgenic lines as compared to the number of lignified cells seen in wild type plants.

The extent of lignification in other tissues, for example, in the plant stems is analyzed as described above using toluidine blue staining. The results indicate that lignification in other tissues such as stem is reduced in transgenic plants constitutively expressing AGL8, as compared to the lignification in wild type plants.

These results indicate that ectopic expression of AGL8 can reduce lignification in transgenic Arabidopsis.

EXAMPLE II

Production of an Arabidopsis agl1 agl5 Double Mutant Displaying Reduced Lignification This example describes the production of an agl1 agl5 double mutant displaying reduced lignification.

A. Production of an agl5 mutant by homologous recombination

A PCR-based assay of transgenic plants was used to identify targeted insertions into AGL5 as described in Kempin et al., Nature 389:802–803 (1997), which is incorporated herein by reference. The targeting construct consisted of a kanamycin-resistance cassette that was inserted between approximately 3 kb and 2 kb segments representing the 5' and 3' regions of the AGL5 gene, respectively. A successfully targeted insertion produces a 1.6 kb deletion within the AGL5 gene such that the targeted allele encodes only the first 42 of 246 amino acid residues, and only 26 of the 56 amino acids comprising the DNA-binding MADS-domain. The recombination event also results in the insertion of the 2.5 kb kanamycin-resistance cassette within the AGL5 coding sequence.

750 kanamycin-resistant transgenic lines were produced by Agrobacterium-mediated transformation, and pools of transformants were analyzed using a PCR assay as described below to determine if any of these primary transformants had generated the desired targeted insertion into AGL5. A single line was identified that appeared to contain the anticipated insertion, and this line was allowed to self-pollinate to permit further analyses in subsequent generations. Genomic DNA from the homozygous mutant plants was analyzed with more than four different restriction enzymes and by several distinct PCR amplifications, and all data were consistent with the desired targeting event. The regions flanking the AGL5 gene also were analyzed to verify that there were no detectable deletions or rearrangements of sequences outside of AGL5.

The kanamycin-resistance cassette within the AGL5 targeting construct contains sequences that specify transcription termination such that little or no AGL5 RNA was expected in the homozygous mutant plants. Using a probe specific for the 3' portion of the AGL5 cDNA, AGL5 transcripts were detected in wild-type but not in agl5 mutant plants. These data indicate that the targeted disruption of the AGL5 gene represents a loss-of-function allele.

Characterization of the agl5 line indicated that the phenotype of this transgenic was not different from wild type Arabidopsis.

The AGL5 knockout (KO) construct was prepared in vector pZM104A, which carries the kanamycin-resistance cassette flanked by several cloning sites (Miao and Lam, Plant J. 7:359–365 (1995), which is incorporated herein by reference). Vector pZM104A also contains the gene encoding β-glucuronidase (GUS), which allows the differentiation of non-homologous from homologous integration events. The 3 kb region representing the 5' portion of AGL5 was obtained by PCR amplification using primer SEQ ID NO:11 (5'-CGGATAGCTCGAATATCG-3') and primer SEQ ID NQ;12 (5'-AACCATTGCGTCGTTTGC-3'). The resulting fragment was cloned into vector pCRII (Invitrogon), and an EcoRI fragment excised and inserted into the EcoRI site of pZM104A. The 3' portion of AGL5 was excised as an XbaI fragment from an AGL5 genomic clone in the vector pCIT30 (Ma et al., Gene 117:161–167 (1992), which is incorporated by reference herein) and inserted into the XbaI site of pZM104A. The resulting plasmid, designated AGL5 KO, was used in Agrobacterium-mediated infiltration of wild-type Arabidopsis plants of the Columbia ecotype. The knockout construct was derived from Landsberg erecta genomic DNA.

Plants containing a homologous recombination event at the AGL5 genomic locus were identified as follows. Approximately 750 primary (T1) kanamycin-resistant transformants were selected, and DNA was extracted from individual leaves in pools representing ten plants as described in Edwards et al., Nucleic Acids Research 19:1349 (1991), which is incorporated by reference herein. To identify a pool that contained a candidate targeted disruption, isolated DNAs were subjected to PCR amplification using primer SEQ ID NO:13 (5'-GTAATTACCAGGCAAGGACTCTCC-3'), which represents AGL5 genomic sequence that is not contained within the AGL5 KO construct, and primer SEQ ID NO:14 (5'-GTCATCGGCGGGGGTCATAACGTG-3'), which is specific for the kanamycin-resistance cassette. Amplified products were size fractionated on agarose gels, and used for standard DNA blotting assays with probe 1. One pool of ten plants revealed the anticipated hybridizing band of the correct size, and this pool was subsequently broken down into individual plants. A single (T1) plant was identified that appeared to contain the desired event, and this plant was allowed to self-pollinate for analyses in subsequent generations. This T1 plant was shown to contain the GUS-reporter gene, indicating that in addition to the putative homologous integration event, there were independent non-homologous events. Segregation in the subsequent generations allowed the identification of plants that no longer contained the GUS-reporter gene, and it was these lines that were used for subsequent analyses.

Plants homozygous for the disruption were identified by PCR amplification using primers SEQ ID NO:15 (5'-GAGGATAGAGAACACTACGAATCG-3') and SEQ ID NO:16 (5'-CAGGTCAAGTCAATAGATTC-3'), which yielded a single 1.5 kb product in wild type plants, and a single 2.6 kb product in the mutant. Further confirmation that these plants contained the desired disruption was obtained by PCR amplification with primers SEQ ID NO:17 (5'-CAGAATTTAGTGAATAATATTG-3') and SEQ ID NO:14, which gave the expected amplified product in the mutant but no product in wild-type plants.

To confirm that the desired disruption had occurred, a series of genomic DNA blots representing wild-type and homozygous mutant (T4 generation) plants were analyzed. Probe 1 hybridized to the expected 3.9 kb XbaI fragment in wild-type and mutant plants, whereas the 1.3 kb XbaI fragment was present only in wild-type. This same probe hybridized to a 6 kb EcoRI fragment in wild-type and to the expected 4.1 and 2.8 kb EcoRI fragments in the mutant. Additional digests with BglII and with HindIII confirmed that the mutant plants contained the desired targeted event. To confirm that there were no detectable deletions or rearrangements outside the targeted region, genomic DNA blots of wild type and homozygous mutant plants were further analyzed. Probe 2 hybridized in wild-type and mutant DNAs to the expected 2.9 kb XmnI fragment, the 1.5 kb and 0.4 kb HincII fragments, and the 0.6 kb HindIII fragment. Probe 3 hybridized in wild-type and mutant DNAs to the 9 kb ScaI fragment, the 3.9 kb XbaI fragment, and the 1.8 kb NdeI fragments. The faintly-hybridizing bands in the ScaI digests represent fragments that span the insertion site, and are, as expected, different sizes in wild-type and agl5 mutant plants.

RNA blotting analyses were performed as follows. Approximately 6 μg of polyA+RNA was purified using DYNABEADS (Dynal) from wild-type and agl5 mutant inflorescences, size fractionated and hybridized using standard procedures (crawford et al., *Proc. Natl. Acad. Sci. USA* 83:8073–8076 (1986), which is incorporated herein by reference) using a gel-purified 450 bp HindIII-EcoRI fragment from pCIT2242 (Ma et al., supra, 1991) specific for the 3' end of the AGL5 cDNA. The same filter was subsequently stripped and re-hybridized with a tubulin-specific probe (Marks et al., *Plant Mol. Biol.* 10:91–104 (1987), which is incorporated herein by reference). Hybridization with the tubulin probe verified that approximately equal amounts of RNA were present in each lane.

B. Production of an agl1 mutant

A PCR-based screen was used to identify a T-DNA insertion into the AGL1 gene essentially as described in Krysan et al., supra, 1996.

RNA blotting analyses demonstrated that AGL1 RNA was not expressed. The agl1 mutant displayed essentially a wild type phenotype.

C. Production and characterization of an agl1 agl5 double mutant agl1 agl5 double mutants were generated by crossing the agl1 and agl5 single mutants. RNA blotting experiments of the agl1 agl5 double mutant are performed as described above. The results indicate that neither AGL1 nor AGL5 RNA is expressed in the agl1 agl5 double mutant.

Toluidine blue analysis of the agl1 agl5 double mutant showed that patches of lignified cells adjacent to the dehiscence zone, which normally are present in wild type plants, are absent in agl1 agl5 mutant fruit although lignification of the fifth valve cell layer was not affected see FIG. 3). These results were further confirmed by lignin-specific histochemical analysis with phloroglucinol, performed as described above. These results indicate that suppression of AGL1 expression combined with suppression of AGL5 expression results in a non-naturally occurring plant variety exhibiting an absence of lignification in certain cells.

EXAMPLE III

Production of an agl8 Mutant Arabidopsis Plant Displaying Enhanced Lignification This example describes methods for producing a non-naturally occurring plant characterized by enhanced lignification due to suppression of AGL8 expression.

A. Production of an agl8 mutant

A mutation designated ful-1 was identified using large scale insertional mutagenesis with enhancer and gene trap Ds transposable elements (Sundarsen et al., supra, 1995; Springer et al., *Science* 268:877–890 (1995), each of which is incorporated herein by reference). This system utilized the maize Ac/Ds transposable elements and the reporter gene GUS. Transposition events were selected and screened for reporter gene expression patterns and mutant phenotypes. The ful-1 mutant was identified in the F3 progeny of an enhancer trap line. Backcrossing to wild type Landsberg erecta confirmed that ful-1 is a recessive mutation.

To address whether the ful-1 mutation was caused by insertion of the Ds-GUS enhancer trap element (DsE), cosegration between the mutant phenotype and expression of the GUS reporter gene was analyzed. Among a total of 200 mutant plants all were GUS positive, and one-third of the wild type plants were GUS negative as expected in the case of complete linkage between the GUS reporter and the mutation. Genomic analysis revealed that the mutant plant carried a single transposed Ds element, as expected.

Sequence analysis showed that the Ds element had inserted into the untranslated leader of the AGL8 gene. Using a probe from the coding region, AGL8 mRNA was not detectable in flowers from homozygous ful-1 mutant plants on RNA blots. The DsE insertion abolished AGL8 gene expression, indicating that ful-1 leads to a complete loss of AGL8 function. Thus, ful-1 is an agl8 mutant.

B. Characterization of lignification in an agl8 mutant

The lignification pattern in agl8 fruits was examined by looking at lignin autofluorescence by methods described above. Whereas wild-type fruits (stage 17) show lignification of valve margin cells adjacent to the dehiscence zone and of the fifth valve cell layer, agl8 fruits displayed additional ectopic lignification of the internal valve mesophyll layers.

These results indicate that suppression of AGL8 expression can produce plants characterized by enhanced lignification.

EXAMPLE IV

Production of 35S::AGL1 and 35S::AGL1 35S::AGL5 Transgenic Plants Displaying Enhanced Lignification This example describes methods for producing transgenic Arabidopsis plants characterized by enhanced lignification due to constitutive expression of AGL1 or constitutive expression of AGL1 and AGL5.

A. Production of transgenic plants expressing AGL1 or AGL5 under control of the CaMV 35S promoter Transgenic 35S::AGL1, 35S::AGL5 and 35S::AGL1 35S::AGL5 plants were generated as follows. A full length AGL1 cDNA was created by fusing the EcoRI fragments of pCIT2241 and pCIT4219 (Ma et al., supra, 1991). The AGL1 cDNA was subsequently cloned into the BamHI site of pCGN18 (Jack et al., *Cell* 76:703–716 (1994)) such that AGL1 transcription was under control of the viral 35S promoter (Benfey and Chua, supra, 1990).

A full-length AGL5 cDNA was PCR amplified with oligonucleotide primers SEQ ID NO:18 (5'-GGAGATCTGAATTCATCTTCCCATCC-3') and SEQ ID NO:19 (5'-CCGGTACCTCAAACAAGTTGCAGAGGTG-GTTGGTCTTGGTTGG ACGAATTCTGATTCGGTTCAAG-3') using pCIT2242 (Ma et al., supra, 1991) as template. After cloning this product into the TA vector (Invitrogen), a BglII/KpnI fragment containing the AGL5 cDNA was cloned into the plant transformation vector pMON530 (Monsanto). In the resulting construct, AGL5 transcription was under control of the 35S promoter. Transgenic plants were selected on kanamycin after Agrobacterium-mediated transformation as described above (Bechtold et al., supra, 1993). 35S::AGL1 transgenic plants were of the Landsberg erecta ecotype, while 35S::AGL5 plants were of the Columbia ecotype. 35S::ACL1 and 35S::AGL5 plants were crossed to each other; in the F1 generation, 352::AGL1 35S::AGL5 plants were identified by polymerase chain reaction genotyping using the AGL1 transgene-specific oligonucleotides SEQ ID NO:20 (5'-GAAGGTGGGA GTAGTCACGAC-3') and SEQ ID NO:21 (5'-CGGAAGGAGGGTTGACGGCA-3') and the AGL5 transgene-specific oligonucleotides SEQ ID NO:22 (5'-GGTGGTGCGAGTAATGAAGTA-3') and SEQ ID NO:23 (5'-TGGTCGGAGGGTTAACGGCG-3').

B. Characterization of lignification in 35S;:AGL1, 35S::AGL5, and 35S::AGL1 35S::AGL5 transgenic plants Lignification was characterized in Arabidopsis fruits that ectopically express AGL1, AGL5 or both. Lignification of 35S::AGL5 fruits appeared identical to that of wild type fruits. However, 35S::AGL1 and 35S::AGL5 fruits (stage 17) displayed ectopic lignification of the valve mesophyll layers, with the most extensive lignification apparent in 35S::AGL1 35S::AGL5 fruits. Cells at positions corresponding to the mesophyll layers are lignified at the valve margin of wild type fruits, indicating that ectopic lignification of 35S::AGL1 35S::AGL5 valve mesophyll layers is a consequence of an acquired valve margin cell identity. The ectopic lignification of the valve mesophyll layers was similar to that seen in agl8 mutants.

These results indicate that a plant ectopically expressing AGL1, or ectopically expressing ACL1 and AGL5, displays enhanced lignification.

EXAMPLE V

Characterization of agl8 agl1 agl5 Triple Mutants

This example describes analysis of a agl8 agl1 agl5 triple mutant.

agl1 agl5 plants were crossed to agl8 mutant plants, and the triple mutants examined in the F3 generation. In addition, agl1 agl5 GT140 plants were crossed to agl8 mutants, and agl1 agl5 agl8 GT140 plants examined in the F3 generation.

Fruits from the agl1 agl5 agl8 triple mutant were quite similar in appearance to fruits from the agl8 single mutant, indicating that AGL8 activity is largely epistatic to that of AGL1 and AGL5. Ectopic lignification was observed in the fruit valves of the triple mutant, although it appears less extensive than that observed in agl8 mutant valves. In addition, the GT140 marker displayed a qualitatively weaker but still expanded domain of expression in the triple mutant.

These results indicate that, while AGL1 and AGL5 can promote lignification of valve margin cells adjacent to the dehiscence zone, and R-like bHLH expression at the valve margin, AGL1 and AGL5 are not absolutely required for either of these functions. AGL8 can directly repress R-like bHLH or other genes promoting lignification of valve margin cells, or can repress an additional factor that is responsible for activating the R-like bHLH transcription factor in the valve margin.

EXAMPLE VI

Characterization of R-like bHLH Expression in Plants With Altered Lignification This example describes expression of the valve margin molecular marker R-like bHLH in an agl1 agl5 double mutant and in plants ectopically expressing AGL1, AGL5, or both.

The GT140 line contains a GUS reporter inserted adjacent to a molecular marker specific to the valve margin, the R-like basic helix-loop-helix transcription factor (R-like bHLH) (Sundaresan et al., supra, 1995); characterization of GUS expression therefore provides a means for following valve margin cell identity when the GT140 line is crossed to mutant or transgenic plants displaying altered lignification.

A. Characterization of R-like bHLH expression in agl8 mutant plants

Figure 6:
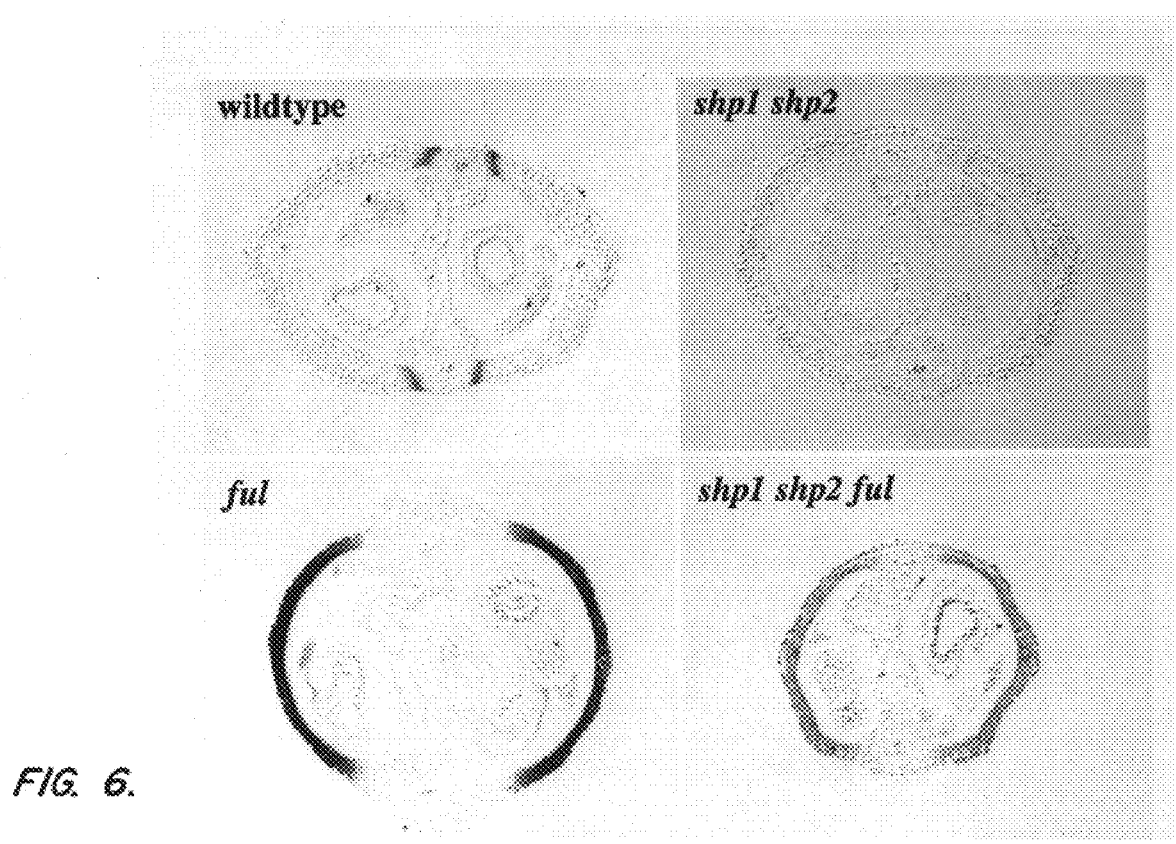
FIG. 6 shows expression of the GT140 valve margin marker (R-like bHLH) in wild-type, agl1 agl5 ("shp1 shp2"), agl8 ("ful"), and agl1 agl5 agl8 ("shp1 shp2 ful") fruits. Transverse sections of wild-type, agl1 agl5, agl8, and agl1 agl5 agl8 fruits (stage 16/17) containing the GT140 molecular marker are shown. In wild-type fruits (A), expression of the GT140 marker occurs in stripes at the valve margin, and these stripes are largely absent in agl1 agl5 fruits (B). Expression of the GT140 marker expands throughout the valves of agl8 fruits (C) and agl1 agl5 agl8 fruits (D), although expression of the marker appears qualitatively weaker in fruits of the triple mutant.

GT140 plants were crossed to agl8 mutant plants characterized by enhanced lignification. As shown in FIG. 6, R-like bHLH expression as indicated by GUS expression appeared in all valve cell layers of agl8 fruits (stage 17), and this expanded domain of expression occurred as soon as the marker was first apparent (stage 13). The expanded domain of R-like bHLH into the valves of agl8 mutant fruits indicates that agl8 valves have acquired the fate of valve margin cells adjacent to the dehiscence zone.

B. Characterization of R-like bHLH expression in 35S::AGL1 35S::AGL5 plants

In contrast to its expression in stripes at the valve margin of wild-type fruits, in 35S::AGL1 35S::AGL5 GT140 fruit, GUS expression was observed throughout the valves, indicating that R-like bHLH was ectopically expressed in the valves. These results indicate that in 35S::AGL1 35S::AGL5 fruit, the valve layers have acquired the identity of valve margin cells adjacent to the dehiscence zone.

C. Characterization of R-like bHLH expression in agl1 agl5 mutant plants

GT140 plants were crossed to agl1 agl5 mutant plants, and GUS expression analyzed. GUS expression was dramatically altered in agl1 agl5 fruits due to the altered fate of agl1 agl5 valve margins. In wild type fruits, GUS was expressed in stripes at the valve margin and in a diffuse domain at the valve base. In contrast, transverse sections of the agl1 agl5 fruits showed that GUS was largely absent from cells at the valve margin, although a low level of expression remained at the base of the valves.

Together, these results indicate that AGL1, AGL5, or both can positively regulate expression of the R-like bHLH transcription factor and that this transcription factor can itself be a positive regulator of lignification. These results further indicate that ectopic expression of R-like bHLH can result in enhanced lignification and that suppression of R-like bHLH in a vascular seed plant can result in reduced lignification.

All journal article, reference, and patent citations provided above, in parentheses or otherwise, whether previously stated or not, are incorporated herein by reference.

Although the invention has been described with reference to the examples above, it should be understood that various modifications can be made without departing from the spirit of the invention. Accordingly, the invention in limited only by the following claims.

We claim:

1. A method of reducing lignification in a vascular plant, the method comprising introducing an exogenous nucleic acid molecule encoding an AGL8-like gene product at least 50% identical to SEQ ID NO:2 into said vascular plant, whereby lignification is reduced due to ectopic expression of said nucleic acid molecule.

2. The method of claim 1, wherein said AGL8-like gene product is at least 75% identical to SEQ ID NO:2.

3. The method of claim 2, wherein said AGL8-like gene product comprises the amino acid sequence of Arabidopsis AGL8 (SEQ ID NO:2).

4. The method of claim 1, wherein said vascular plant is a woody plant.

5. The method of claim 4, wherein said woody plant is selected from the group consisting of Eucalyptus, cottonwood, alder, Douglas fir, Hemlock, pine and spruce.

6. The method of claim 1, wherein said vascular plant is a leguminous plant.

7. The method of claim 6, wherein said leguminous plant is selected from the group consisting of alfalfa, clover, lucerne, birdsfoot trefoil, Stylosanthes, *Lotononis bainessii* and sainfoin.

8. The method of claim 1, wherein said vascular plant is a forage grass.

9. The method of claim 8, wherein said grass is selected from the group consisting of bahiagrass, bermudagrass, dallisgrass, pangolagrass, big bluestem, indiangrass, switchgrass, smooth bromegrass, orchardgrass, timothy, Kentucky bluegrass and tall fescue.

10. The method of claim 1, wherein said exogenous nucleic acid molecule encoding an AGL8-like gene product is operatively linked to an exogenous regulatory element.

11. The method of claim 10, wherein said exogenous regulatory element is a constitutive regulatory element.

12. The method of claim 10, wherein said exogenous regulatory element is a tissue-selective regulatory element.

13. The method of claim 12, wherein said tissue-selective regulatory element is an AGL1 regulatory element or AGL5 regulatory element.

14. The method of claim 12, wherein said tissue-selective regulatory element is a lignified tissue-selective regulatory element selected from the group consisting of a fiber-selective regulatory element, xylem-selective regulatory element and a tracheid selective regulatory element.

15. A transgenic vascular plant characterized by reducing lignification, the transgenic vascular plant comprising an ectopically expressed nucleic acid molecule comprising a lignified tissue-selective regulatory element operatively linked to a nucleic acid molecule encoding an AGL8-like gene product at least 50% identical to SEQ ID NO:2.

16. The transgenic vascular plant of claim 15, wherein said AGL8-like gene product is at least 75% identical to SEQ ID NO:2.

17. The transgenic vascular plant of claim 16, wherein said AGL8-like gene product comprises the amino acid sequence of Arabidopsis AGL8 (SEQ ID NO:2).

18. The transgenic vascular plant of claim 15, wherein said lignified tissue-selective regulatory element is selected from the group consisting of a fiber-selective regulatory element, xylem-selective regulatory element and a tracheid selective regulatory element.

19. A tissue derived from the transgenic vascular plant of claim 15, said transgenic vascular plant comprising an ectopically expressed nucleic acid molecule comprising a lignified tissue-selective regulatory element operatively linked to a nucleic acid molecule encoding an AGL8-like gene product at least 50% identical to SEQ ID NO2.

20. A kit for producing a transgenic vascular plant characterized by altered lignification, comprising a nucleic acid molecule comprising a lignified tissue-selective regulatory element and a nucleic acid molecule encoding an AGL8-like gene product at least 50% identical to SEQ ID NO:2.

21. The kit of claim 20, wherein said lignified tissue-selective regulatory element is selected from the group consisting of a xylem-selective regulatory element, tracheid-selective regulatory element and fiber-selective regulatory element.

22. The method of claim 1, wherein said AGL8-like gene product is at least 90% identical to SEQ ID NO:2.

23. The transgenic vascular plant of claim 15, wherein said AGL8-like gene product is at least 90% identical to SEQ ID NO:2.

* * * * *